(12) United States Patent
Matsunaga et al.

(10) Patent No.: US 6,484,438 B2
(45) Date of Patent: Nov. 26, 2002

(54) PEST CONTROL DEVICE AND VOLATILE SUBSTANCE HOLDER FOR USE IN SAME

(75) Inventors: Tadahiro Matsunaga, Kobe (JP); Tomonori Iwasaki, Sanda (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 09/966,799

(22) Filed: Oct. 1, 2001

(65) Prior Publication Data

US 2002/0062593 A1 May 30, 2002

(30) Foreign Application Priority Data

Oct. 4, 2000 (JP) ........................................ 2000-305481

(51) Int. Cl.⁷ ............................................. A01M 19/00
(52) U.S. Cl. ........................................................ 43/129
(58) Field of Search ................................ 43/132.1, 129, 43/124

(56) References Cited

U.S. PATENT DOCUMENTS

| | | | |
|---|---|---|---|
| 667,469 A | * 2/1901 | Tighe | |
| 2,662,332 A | * 12/1953 | McIntire | |
| 3,192,167 A | * 6/1965 | Ogawa et al. | |
| 3,548,533 A | * 12/1970 | Jensen | |
| 3,607,780 A | * 9/1971 | Scott | |
| 3,793,763 A | * 2/1974 | Griffin et al. | |
| 5,335,446 A | * 8/1994 | Shigetoyo | 43/125 |
| 5,566,502 A | * 10/1996 | Shigetoyo | 43/125 |
| 5,829,188 A | * 11/1998 | Tanitomi | 43/129 |
| 6,225,495 B1 | 5/2001 | Ujihara et al. | |

FOREIGN PATENT DOCUMENTS

| | | | | |
|---|---|---|---|---|
| DE | 4025828 | * 2/1992 | | 43/124 |
| JP | 63058 | * 4/1985 | | 43/132.1 |
| JP | 05-068459 | 3/1993 | | |
| JP | 406153752 | * 6/1994 | | 43/124 |
| JP | 07-236399 | 9/1995 | | |
| JP | 08-000147 | 1/1996 | | |
| WO | WO 84/01264 | * 4/1984 | | 43/124 |

* cited by examiner

Primary Examiner—Thomas Price
(74) Attorney, Agent, or Firm—Nixon & Vanderhye, P.C.; Frank P. Presta

(57) ABSTRACT

A pest control device is provided with (1) a volatile substance holder, which includes a pest control component volatilization surface and a liquid volatilization surface, and (2) an indicator, which is composed of a wick and a bottle. The pest control component volatilization surface holds a pest control component volatile at ordinary temperature so that the pest control component can be volatilized into the air, while the liquid volatilization surface is able to hold a liquid volatile so that the liquid can be volatilized into the air. The wick is for supplying the liquid to the liquid volatilization surface of the volatile substance holder, while the bottle contains the liquid to be supplied to the liquid volatilization surface via the wick. In this manner, the indicator indicates how much the pest control component, which is volatilized from the pest control component volatilization surface is left, by showing how much the liquid is left in the bottle.

16 Claims, 14 Drawing Sheets

FIG. 5
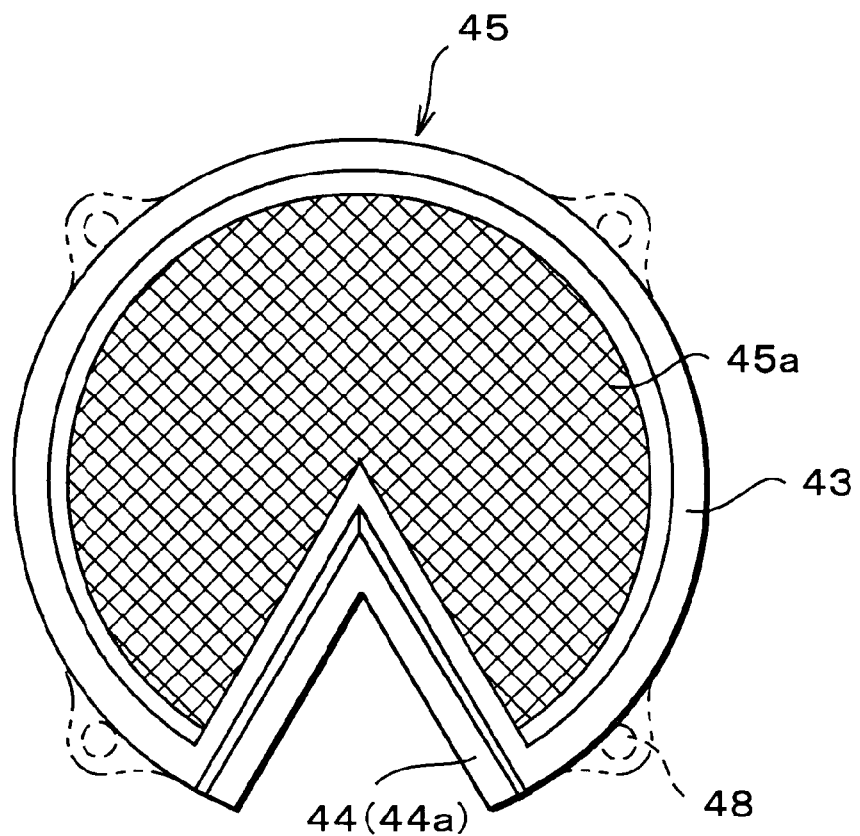
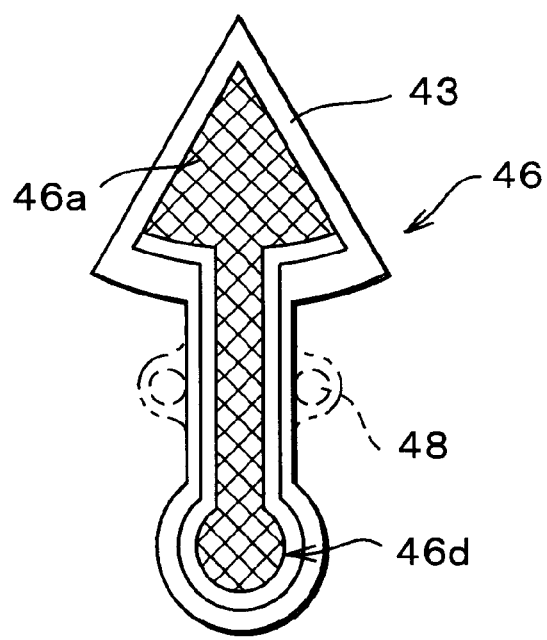

F I G. 1 0 (a)　　F I G. 1 0 (b)
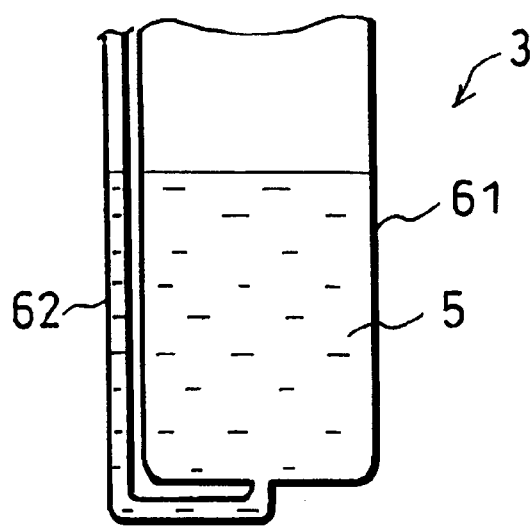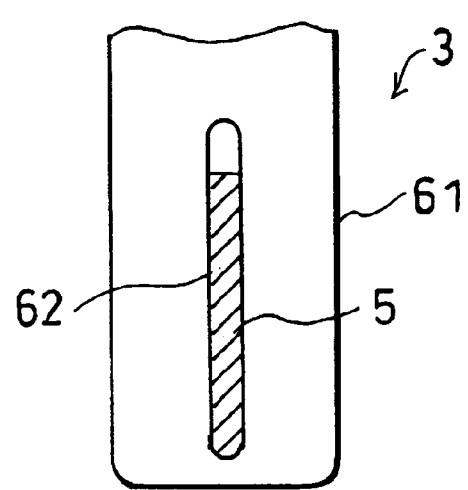

PEST CONTROL DEVICE AND VOLATILE SUBSTANCE HOLDER FOR USE IN SAME

FIELD OF THE INVENTION

The present invention relates to a pest control device and a volatile substance holder for use in same. Particularly, the present invention relates to a pest control device of a non-heating type, which volatilizes into the air a pest control component, such as a pesticidal component or a pest repellent component, which are volatile at ordinary temperature, and a volatile substance holder for use in same.

BACKGROUND OF THE INVENTION

A pest control device, which has been developed recently to replace a pest control device of a heating type, uses a fan to air a holder, such as paper, in which absorbed is a pest control agent whose active component is a pesticidal component or a pest repellent component that are volatile at ordinary temperature, thereby volatilizing the active component into the air so as to control the pest (Japanese Un-Examined Patent Publication, Tokukaihei, No. 7-236399: published on Sep. 12, 1995).

Moreover, Japanese Un-Examined Patent Publication, Tokukaihei, No. 5-68459 (published on Mar. 23, 1993) discloses a pest control device, which volatilizes an active component into the air by using driving means to rotate a holder itself, which has absorbed a pest control agent.

Those pest control devices need no heating means for volatilizing the pest control agent, unlike the pest control device of the heating type, thereby having low energy consumption. For this reason, a fan of the pest control devices can be driven by using a dry battery and the like, without using a commercial power supply. Therefore, the pest control devices have excellent compatibility, while the pest control devices are excellently safe, because the pest control devices themselves and their surroundings are prevented from being heated, thereby eliminating possibilities of burning and fire.

However, when the pest control agent is absorbed in the holder in this way, a user has no way to check how much an active component of the pest control agent remains, because the active component of the volatile pest control agent, which is volatilized from the holder, is invisible. Therefore, the user cannot determine when the holder runs out of the active component of the pest control agent and has no efficacy anymore (hereinafter, the loss of the efficacy due to the running out of the active component is referred to as an end of the efficacy). Thus, the user should refer to a serviceable time that is roughly estimated. However, depending on how frequently the holder is used, or how the user judges, the user may judge that the holder is finished even the holder can be still used efficaciously, or the user may decide to continue to use the holder even after the end of the efficacy has come.

Therefore, there is a need to develop means that surely determines reduction or an end point (the end of efficacy) of the active component of the pest control agent.

A well-known conventional methods of determination of the end point is, for example, a method in which the amount of the active component of the pest control agent is adjusted in accordance with a service life of a dry battery so that an end of the service life of the dry battery indicates an end of the active component absorbed in paper, thereby informing a user a time to exchange the paper.

However, the method in which the end of the efficacy is indicated by the end of the service life of the dry batter has such problems that the end of the efficacy and the end of the service life of the dry battery often do not synchronize with each other, because the active component of the pest control agent is not reduced always in a synchronizing manner with the usage of the dry battery. Further, the end of the service life of the dry battery also merely indicates in approximation how long the holder can be used, because there is no way to see the reduction of the active component of the pest control agent. Therefore, the user may be informed of the end of the efficacy by the end of the service life of the dry battery long after the active component has run out, and the holder has lost its efficacy.

To overcome the problems, suggested is a method in which the reduction or the end point of the active component of the pest control agent to be volatilized can be checked by looking at how much the active component is left. For example, Japanese Un-Examined Patent Publication, Tokukaihei, No. 8–147 (published on Jan. 9, 1996) discloses a method in which an pest control agent or a holder of it is colored, so that a time to exchange the holder is indicated by disappearance of the color.

However, while the method of in which a pest control agent or a holder of it is colored allows a user to see and judge the color, the color is not color of the active component itself, but the color of a pigment added. The color disappears with a lapse of time, for example, due to a chemical change, and a period of time for the color to disappear is merely adjusted to the period of time for the active component of the pest control agent to vanish. In other words, there is no physical interrelationship between the volatilization of the active component of the pest control agent and the change of the color of the pigment. Because of this, in the above method, it is impossible to have a good synchronization between the running out of the active component (the end of the efficacy) of the pest control agent and the disappearance of the color of the holder, while it is hard to adjust timing of the color disappearance subtly to attain the good synchronization, thus posing a problem that it is hard to control the end point.

Moreover, every user differently judges the end point from the color disappearance, while the color may change with speckles, or may not disappear completely, thereby making it difficult to judge the end point from the color change. For those reason, while some users may judge it is time to exchange the holder, the others may not judge so and continue to use the holder. To conclude, none of the methods can provide the users with means to surely determine the end point.

Conventionally, as a pest control device that can surely check the reduction and the end point (the end of the efficacy) of the active component of the pest control agent, well known is a pest control device that uses a bottle to contain a pest control solution, in which a pest control agent is dissolved in a solvent, so that the pest control solution is sucked up and heated in order to volatilize the solvent together with the active component. An example of such pest control device is a pest control device using a liquid mosquito-repellent. This type of the pest control device allows a user to check by sight how much the pest control solution is left.

However, the method of the above pest control device needs heating of the pest control solution. Thus, when a pest control agent, which is volatile at ordinary temperature, is dissolved in a solvent and contained in a bottle so that the pest control solution is sucked up from the bottle and volatilized by wind, for example, use of a solvent having low boiling point, such as ethanol, is impractical because the pest control solution evaporates to disappearance too fast and has a very short service time. On the contrary, use of a solvent having a high boiling point retards the volatilization of the pest control agent, thereby deteriorating efficiency of the pest control.

Furthermore, when the pest control agent is dissolved in the solvent so as to be contained in a bottle and used in the pest control device of the ordinary-temperature volatilization type, as above, the amount of the pest control agent to be volatilized is decreased as a result of the dissolution of the pest control agent in the solvent, thereby limiting efficacy of the pest control agent.

Therefore, there is no pest control device of the non-heating type which allows a user to easily control the end point and to surely check the reduction or the end point (end of efficacy) of the active component of the pest control agent, while using a pest control agent that can volatilize at ordinary temperature. Thus, it is demanded to provide a pest control device that allows a user to easily control the end point and to surely check the reduction or the end point (end of efficacy) of the active component of the pest control agent, while having en excellent pest control efficiency.

SUMMARY OF THE INVENTION

In view of the forgoing problems, the present invention is made to solve the problems. The present invention has objects to provide (a) a pest control device that allows a user to easily control the end point and to surely check the reduction or the end point (end of efficacy) of the active component of the pest control agent, while having an excellent pest control efficiency, and (b) a volatile substance holder for use in same.

The inventors of the present invention, as a result of an intensive study, have solved the forgoing problems. In the present invention, a pest control component, which volatilizes at ordinary temperature, is provided separately from the indicator to show how much the pest control component is left, while the indication how much the pest control component is left, is carried out by indicating how much a liquid, which is volatilized, is left in the indicator, to solve the forgoing problems.

Therefore, in order to attain the above objects, a pest control device of the present invention is provided with (1) a volatile substance holder, including a first and a second volatilization surfaces, the first volatilization surface holding a pest control component so that the pest control component can be volatilized into the air (hereinafter, referred to as the volatilization surface (I)), and the second volatilization surface being able to hold a liquid so that the liquid can be volatilized into the air (hereinafter, referred to as the volatilization surface (II)), where the pest control component and the liquid are volatile at ordinary temperature, and (2) an indicating section, including a liquid supplying system and a liquid containing container, the liquid supplying system supplying the liquid to the volatilization surface (II) of the volatile substance holder, and the liquid containing container containing the liquid to be supplied to the volatilization surface (II) via the liquid supplying system, wherein the indicating section indicates how much the pest control component to be volatilized from the volatilization surface (I) is left in the volatile substance holder by showing how much the liquid is left in the liquid containing container.

With the above arrangement, the volatile substance holder is provided with two volatilization surfaces so as to hold and volatilize the pest control component and the liquid on the separate volatilization surfaces. This optimizes efficiency of the pest control component because the pest control component is volatilized without retardation.

Moreover, with the above arrangement, the pest control agent and the indicator for indication are separately disposed, while the pest control agent and the indicator are correlated with each other. This makes it easy to control the end point (the end of efficacy) of the pest control component and to adjust volatilization of the pest control component in terms of quantity, thereby arbitrarily and easily setting the disappearance point of the liquid and the end point of the pest control component.

Moreover, the above arrangement allows the user to know by sight how much the pest control component is left (or reduced).

Therefore, the above arrangement provides a pest control device that attains a high efficiency in the controlling, and easily controls the end point of the pest control component, while allowing the user to surely check the reduction and the end point of the pest control component.

Furthermore, with the above arrangement, for example, another chemical may be added in the liquid, if necessary, so that the indicator can functions as an indicator and as a container of the chemical. This makes it possible that the pest control agent is used in association with a chemical, which may be highly volatile or low volatile compared with the pest control component, or may be a solid. Further, the above arrangement precisely synchronizes an end of efficacy of the pest control component and that of the chemical, with ease. This allows the pest control device to have various additional functions to combine with in accordance with needs of a user, such as a deodorizing function, an antibacterial function, and a fragrance function. Meanwhile, a service life of the pest control device until the end of efficacy of its active component can be arbitrarily set.

Moreover, a volatile substance holder of the present invention is provided with a first and a second volatilization surfaces, the first volatilization surface holding a pest control component so that the pest control component can be volatilized into the air (i.e., the volatilization surface (I)), and the second volatilization surface being able to hold a liquid so that the liquid can be volatilized into the air (i.e., the volatilization surface (II)), where the pest control component and the liquid are volatile at ordinary temperature.

With the above arrangement, the volatile substance holder is provided with two volatilization surfaces so as to hold and volatilize the pest control component and the liquid in the separate volatilization surfaces. This optimizes efficiency of the pest control component because the pest control component is volatilized without retardation, while including the pest control component not in the indicator that carries out the indication by using the liquid. Therefore, the above arrangement provides the volatile substance holder that is necessary for providing the pest control device that attains a high efficiency in the pest controlling, and easily controls the end point of the pest control component, while allowing the user to surely check the reduction and the end point of the pest control component.

It is preferable that the volatile substance holder holds a compound in a pyrethroid group in the volatilization surface (1), so that it is possible to provide the pest control device that is excellent in volatilization of the pest control component and in the pest control activity.

For a fuller understanding of the nature and advantages of the invention, reference should be made to the ensuing detailed description taken in conjunction with the accompanying drawings.

BRIEF DESCRIPTION OF THE DRAWINGS

FIG. 5 is a plan view showing another constitution of the pest control component holder of and the liquid holder of the pest control device.

FIG. 10(a) is a cross-sectional view showing constitution of another bottle of the pest control device.

FIG. 10(b) is a front view of the constitution of the another bottle shown in FIG. 10(a).

DESCRIPTION OF THE EMBODIMENTS

Described below is an embodiment in accordance with the present invention, with reference to FIGS. 1 to 14.

Figure 1:
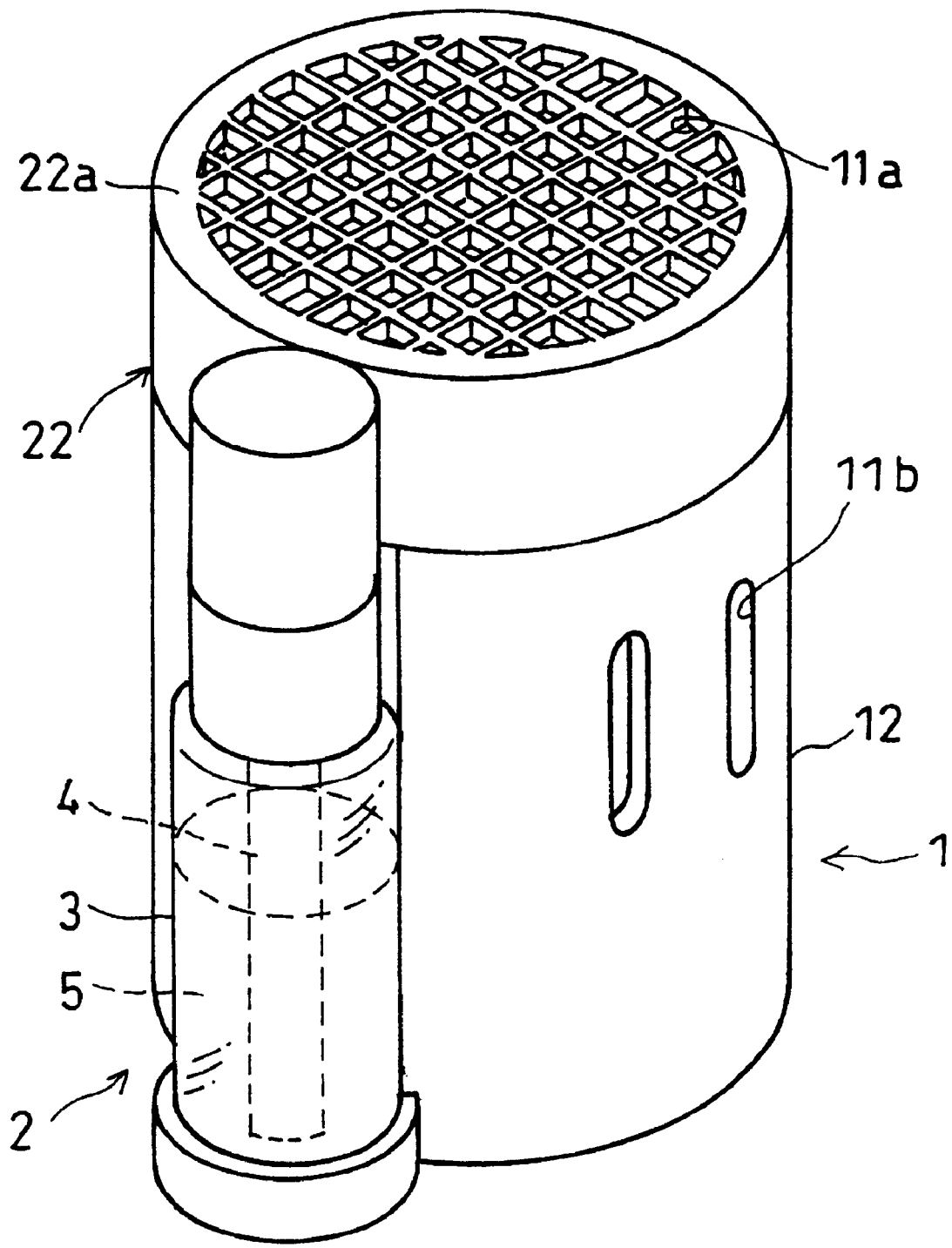
FIG. 1 is a perspective view showing constitution of a pest control device of an embodiment of the present invention.
Figure 2:
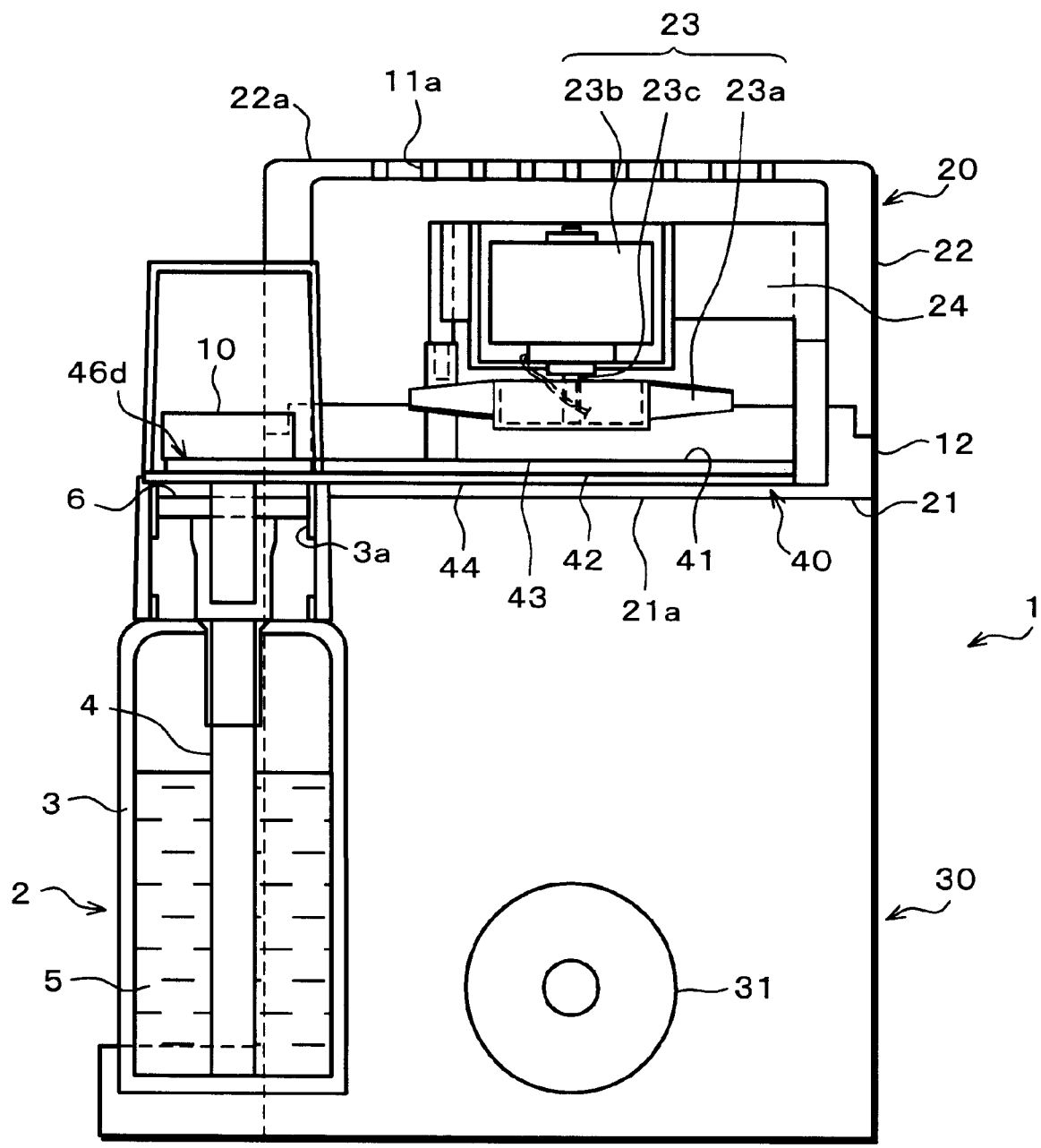
FIG. 2 is a cross-sectional view illustrating the constitution of the pest control device of the embodiment of the present invention.

FIG. 1 is a perspective view of constitution of a pest control device in accordance with the present embodiment, while FIG. 2 is a cross-sectional view of the configuration of the pest control device of the present embodiment.

As shown in FIGS. 1 and 2, the pest control device of the present embodiment is provided with a pest control device main body 1 and an indicator 2 (indicating means).

The pest control device main body 1 is hollow inside, and is provided with a chamber 20, which can vent, and a dry battery holding section 30 that holds a dry battery 31, as shown in FIG. 2. The dry battery holding section 30 is provided with terminals (not shown) to connect with electrodes of the dry battery 31. The terminals are connected, via a control circuit (not shown), to a motor 23b of an air stream generator 23 (air stream generating means) (will be explained later) that is disposed in the chamber 20.

On the other hand, the chamber 20 is provided with a pedestal 21 and a lid 22, which is removable. Inside the chamber 20, disposed are the air stream generator 23, which generates an air stream inside the chamber 20, and a volatile substance holder 40.

The air stream generator 23 is provided with an air fan 23a, a motor 23b, which rotates the air fan 23a, and a supporting shaft 23c. The motor 23b drives the air fan 23a to rotate. The air fan 23a is attached to the motor 23b by the supporting shaft 23c. The motor 23b is fixed in the pedestal 21 by a motor supporting frame 24. The air fan 23a is disposed so as to face a volatile substance volatilization surface 41 of the volatile substance holder 40. In the pest control device shown in FIG. 2, the air fan 23a is disposed above the volatile substance holder 40, and is attached to the motor 23b, which is above the air fan 23a, by the supporting shaft 23c.

Moreover, as shown in FIG. 1, a vent hole 11b, which acts as an air inlet, is disposed, for example, on a side wall 12 of the pest control device main body 1. On a ceiling 22a of the lid 22, a vent hole 11a, which functions as an air exit, is disposed. Because of this, in the pest control device shown in FIG. 2, the air stream generator 23 inhales air via the vent hole 11b and exhausts a volatile substance (a volatile component), which volatilizes from the volatile substance volatilization surface 41 of the volatile substance holder 40, through the vent hole 11a to an exterior of the pest control device main body 1.

The volatile substance holder 40 is so supported by the pedestal 21 that the volatile substance holder 40 is removable. As shown in FIG. 2, the pedestal 21 is, for example, provided with a projected platform 21a horizontally, which is extended from the side wall 12 of the pest control device main body 1, inwardly with respect to the pest control device main body 1. The volatile substance holder 40 is mounted on the projected platform 21a, as shown in FIGS. 2 and 3.

As shown in FIG. 2, the volatile substance holder 40 is provided with such an arrangement in which the volatile substance holding material 42 is sandwiched by a pair of volatile substance holder fixing sections, namely an upper frame 43 and a lower frame 44.

Figure 3:
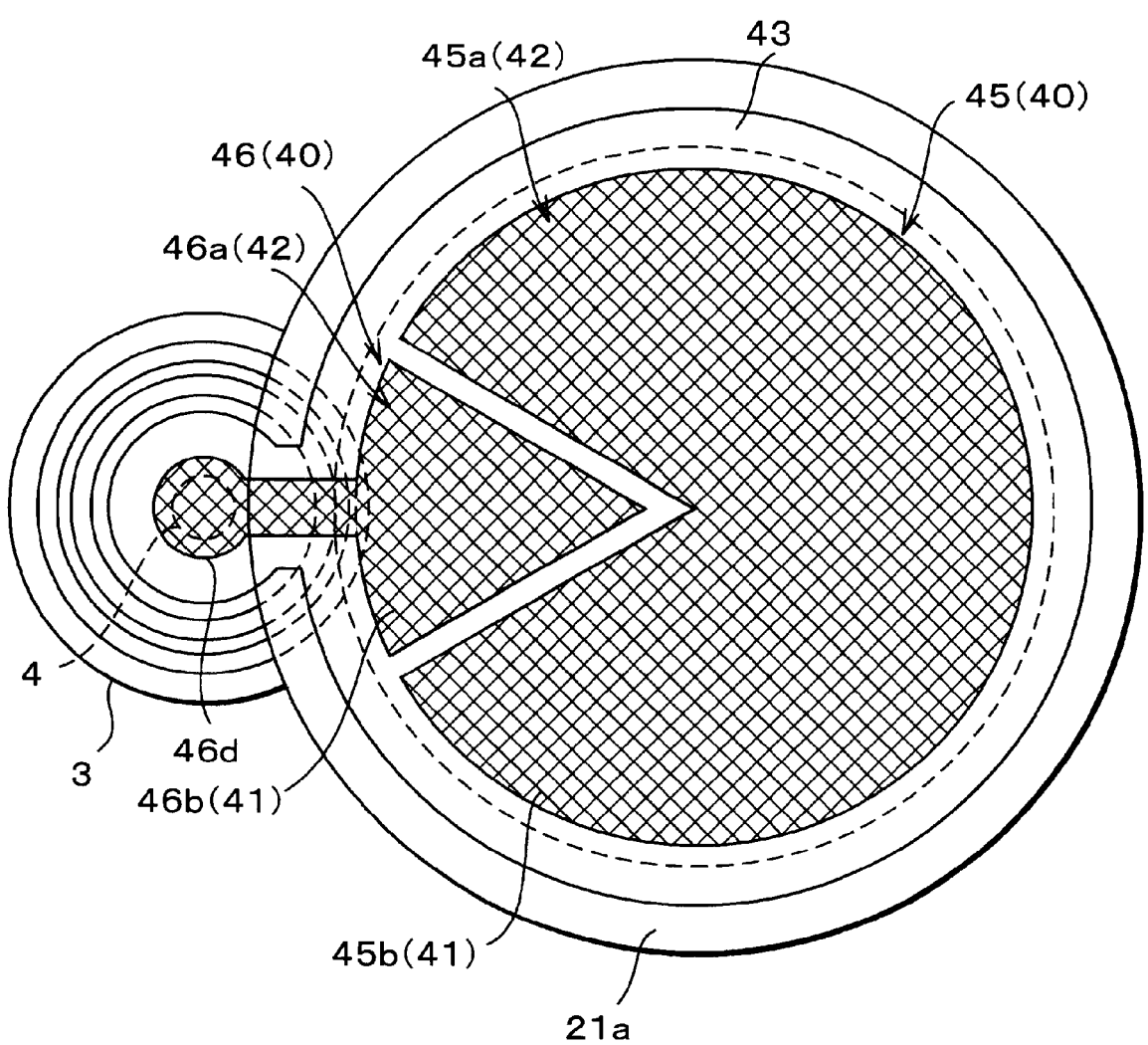
FIG. 3 is a plan view showing main parts of the pest control device.

Moreover, the volatile substance holder 40, as shown in FIGS. 3, 4(a), and 4(b), is composed of a pest control component holder (pest control component holding section) 45 and a liquid holder (liquid holding section) 46. The pest control component holder 45 holds the pest control component, such as a pesticidal component or a pest-repellant component. The liquid holder 46 holds a liquid 5 (see FIGS. 1 and 2) that is supplied from the indicator 2.

In FIG. 4(a) and 4(b), a constitution of the volatile substance holder 40 is illustrated in detail. FIG. 4(a) is a plan view showing constitutions of the pest control component holder 45 and the liquid holder 46, which constitute the volatile substance holder 40, while FIG. 4(b) is a plan view illustrating a constitution of a volatile substance holder supporting frame 47, which supports the pest control component holder 45 and the liquid holder 46.

The pest control component holder 45 and the liquid holder 46 are disposed independently from each other. Thus, a pest control component holding material 45a, which is a volatile substance holding material 42 of the pest control component holder 45, does not touch a liquid holding material 46a, which is the volatile substance holding material 42 of the liquid holder 46. In other words, a pest control component volatilization surface 45b (a volatilization surface (I)), which is the volatile substance volatilization surface 41 of the pest control component holder 45, does not touch a liquid volatilization surface 46b (a volatilization surface (II)), which is the volatile substance volatilization surface 41 of the liquid holder 46.

As shown in FIG. 4(a), the pest control component holder 45a and the liquid holder 46a are, for example, independently sandwiched and supported by volatile substance holding material fixing sections, such as the upper frames 43 and the lower frames 44.

The upper frames 43 and the lower frames 44 are not limited to any specific material, and may be made of any raw material, which can maintain shape of the pest control component holding material 45a and the liquid holding material 46a, and is tolerate against a pest control component, which is held in the pest control component holding material 45a, and a liquid 5 held in the liquid holding material 46a (see to FIGS. 1 and 2). For example, plastic and the like can be used to make the upper frames 43 and the lower frames 44. Note that, the pest control component holding material 45a and the liquid holding material 46a can be respectively fixed by volatile substance holding material fixing section made of different raw materials respectively, in accordance with types of the pest control agent and the liquid 5 to be held.

The pest control component holding material 45a and the liquid holding material 46a, which are sandwiched and held by the upper frames 43 and the lower frames 44 respectively as shown in FIG. 4(a), is placed on the volatile substance holder supporting frame 47, for example, as indicated by a long dashed double-short dashed line in FIG. 4(b). Accordingly, the pest control component holding material 45a and the liquid holding material 46a are, together with the volatile substance holder supporting frame 47, placed on the projected platform 21a of the pedestal 21.

The volatile substance holder supporting frame 47 is provided with a hole 47a and a hole 47b. The hole 47a is in accordance with a shape of the pest control component volatilization surface 45b, while the hole 47b is in accordance with a shape of the liquid volatilization surface 46b. The holes 47a and 47b let air pass through toward the pest control component volatilization surface 45b and the liquid volatilization surface 46b. Moreover, in a boundary area between the hole 47a and hole 47b in the volatilization substance holder supporting frame 47, provided is a projected section 49 (a partition band), which acts as a partition board (a compartment) for keeping separate the pest control component holder 45 and the liquid holder 46 so as not to let the control component holder 45 and the liquid holder 46 touch each other. The projected section 49 is disposed vertically with respect to the volatile substance volatilization surface 41. Note that, FIG. 4(b) illustrates an arrangement where the projected section 49 is disposed only in the boundary area. However, it is also possible to have such an arrangement in which the projected section 49 is extended to an edge of the volatile substance holder supporting frame 47.

The volatile substance holder 40 is not limited to this arrangement. As shown in FIG. 5, it is also possible to have such an arrangement that the lower frame 44, which sandwiches and supports the pest control component holding material 45a is projected out horizontally, or a projected section 44a, which is projected out horizontally from a lower portion of the lower frame 44, is provided in order to support the liquid holder 46. Furthermore, it is also possible to have such an arrangement that the liquid holder 46 is engaged or interlocked with the pest control component holder 45. In this case, the upper frame 43 functions as a compartment (a partition band) for dividing the pest control component volatilization surface 45b and the liquid volatilization surface 46b so as not to let the pest control component volatilization surface 45b and the liquid volatilization surface 46b touch each other.

Furthermore, instead of using the volatile substance holder supporting frame 47, the projected platform 21a of the pedestal 21 having a shape identical to a shape of the volatile substance holder supporting frame 47 can be used.

Moreover, the pest control component holder 45 and the liquid holder 46 need not be associated with the volatile substance holding material fixing section discussed above. It is also possible to use the pest control component holding material 45a and the liquid holding material 46a as the pest control component holder 45 and the liquid holder 46.

Provided that, the pest control component holder 45 and the liquid holder 46 are fixed not to be moved by the air stream generated by the air stream generator 23, the pest control component holding material 45a and the liquid holding material 46a can be placed directly on the volatile substance holder supporting frame 47.

In case the pest control component holding material 45a and the liquid holding material 46a are prepared from different raw materials, it is possible to arrange that the volatile substance holding material fixing section fixes only one of the pest control component holding material 45a and the liquid holding material 46a.

Moreover, in case the pest control component holding material 45a and the liquid holding material 46a are sandwiched by the upper frame 43 and the lower frame 44, the upper frame 43 and the lower frame 44 can be fixed by being screwed by the screw 48 and the like, as indicated by long dashed double-short dashed line in FIG. 4(a), while it is also possible to fix the upper frame 43 and the lower frame 44 by interlocking or bonding them together.

Furthermore, it is possible to arrange that the pest control component holder 45 and the liquid holder 46 are provided with the pest control component holding material 45a and the liquid holding material 46a, and a upper frame placed as a weight on the pest control component holding material 45a and the liquid holding material 46a. The upper frame has a hole shaped in accordance with a shape of the pest control component volatilization surface 45b and the liquid volatilization surface 46b.

Furthermore, where used is a pest control component in a solid form or a solid composition that will be discussed later, or a solidified of the composition, (a) if the air fan 23a of the air stream generator 23 is disposed on an upper side (a side where the vent hole 11a as the an air exit is located) of the volatile substance holder 40, as shown in FIG. 2, so that the pest control component, which has been volatilized from the pest control component volatilization surface 45b, is inhaled by the air stream generator 23, so as to be exhausted through the vent hole 11a out of the pest control device main body 1, (b) alternatively if air is not required to pass through the pest control component holder 45 (that is, no ventilation is required) (for example, if the air stream generator 23 is not necessary (for example, because a pest control component of a natural evaporation (volatilization) type is used)), the volatile substance holder 40 need not have the arrangement for ventilation, as long as the volatile substance holder 40 is provided with two volatilization surfaces for volatilization of the volatile substance into air, while each volatilization surface is so provided that each volatilization surface does not touch each other, and is able to hold the pest control component and the liquid 5, respectively. Thus, for example, it is possible to have such an arrangement that provided is a compartment between the pest control component holding section (the pest control component holder 45) and the liquid holding section (the liquid holder 46), while both of the pest control component holding section and the liquid holding section or only the pest control component holding section is constituted with a tray whose upper part is open to outside.

As discussed above, the pest control component holder 45 may have any arrangement, provided that the pest control component holder 45 holds the pest control component so that the pest control component can be volatilized into the air. However, preferred is such an arrangement that the pest control component holder 45 allows the pest control component to be appropriately volatilized by means of the air stream passing through the pest control component holder 45, as an arrangement where it is easy to control the end point and an operation of the pest control device can be interrupted.

For this reason, it is preferable that the pest control component holding material 45a of the pest control component holder 45 allows the pest control component to be appropriately volatilized by using the air stream passing through the pest control component holding material 45a.

Listed here are examples of raw materials to prepare the pest control component holding material 45a to be used in the pest control component holder 45: paper, non-woven fabric, cloth, sponge, pulp, a resin film, ceramics, porous resin (polypropylene foam, urethane foam, and the like), synthetic fiber (nylon, polyester, polypropyrene, polyethylene, and the like), natural fiber (wool, silk, cotton, hemp, and the like), inorganic fiber (glass fiber and the like), inorganic moldings and products of those materials. Note that, the pest control component holding material 45a is not limited to those examples. Moreover, concerning a material having a sheet-like shape, it is also possible to expand a surface area with respect to volume, by folding, by jointing partially, by processing to a honeycomb-like shape, or by making its surface uneven, if necessary.

It is preferable that the pest control component holding material 45a has a large surface area with respect to volume, in order to constitute the pest control component volatilization surface 45b. Moreover, the pest control component holding material 45a is preferred to have a large gas permeability. For this reason, for example, a net-like shaped or a honeycomb-like shaped material is preferably used for the pest control component holding material 45a. Furthermore, concerning a material having a sheet-like shape, it is also possible to expand a surface area with respect to volume (that is, with respect to the amount of pest control component to be held) by folding, jointing partially, or making its surface uneven, if necessary. Further, it is also preferable to expand the surface area with respect to volume of the liquid holding material 46a, for example, by laminating, by folding, or by partially jointing materials having a net-like shape or a honeycomb-like shape, if necessary.

The pest control component holder 45 (the pest control component holding material 45a) is used while the pest control component is held on the pest control component volatilization surface 45b.

The pest control component of the present invention is not limited to a specific compound, provided that the pest control component can control a pest (that is, has pest control activity), and is volatile at ordinary temperature. However, preferred for the pest control component is a compound in a pyrethroid group, in view of the pest control activity and the volatility.

The compound in the pyrethroid group is a natural pyrethrin or synthetic pyrethroid.

Specific examples of the compound in the pyrethroid group that may be used in the present invention are: 2-methyl-3-allyl-4-oxo-2-cyclopenten-1-yl 3-(2-methyl-1-propenyl)-2,2-dimethycyclopropanecarboxylate, 2-methyl-3-propargyl-4-oxo-2-cyclopenten-1-yl 3-(2-methyl-1-propenyl)-2,2-dimethylcyclopropanecarboxylate, 5-propargyl-2-furfuryl 3-(2-methyl-1-propenyl)-2,2-dimethylcyclopropane carboxylate, 5-propargyl-2-furfuryl 2,2,3,3-tetramethylcyclopropanecarboxylate, 1-ethynyl-2-methyl-2-pentenyl 3-(2-methyl-1-propenyl)-2,2-dimethylcyclopropanecarboxylate, 1-ethynyl-2- methyl-2-pentenyl 3-(2-chloro-2-fluorovinyl)-2,2-dimethylcyclopropane-1-carboxylate, 2,3,5,6-tetrafluoro-4-methylbenzyl 3-(2-methyl-1-propenyl)-2,2-dimethylcyclopropanecarboxylate, 2,3,5,6-tetrafluoro-4-methylbenzyl 3-(2-chloro-2-fluorovinyl)-2,2-dimethylcyclopropanecarboxylate, 2,3,5,6-tetrafluorobenzyl 3-(2,2-dichlorovinyl)-2,2,-dimethylcyclopropane carboxylate, 2,3,5,6-tetrafluoro-4-methylbenzyl 3-(1-propenyl)-2,2-dimethylcyclopropanecarboxylate, 2,3,5,6-tetrafluoro-4-methylbenzyl 3-(2,2-dichlorovinyl)-2,2-dimethylcyclopropanecarboxylate, 2,3,5,6-tetrafluoro-4-methoxybenzyl 3-(2,2-dichlorovinyl)-2,2-dimethylcyclopropanecarboxylate, 2,3,5,6-tetrafluoro-4-methoxybenzyl 3-methoxyiminomethyl-2,2-dimethylcyclopropanecarboxylate, 2,3,5,6-tetrafluoro-4-methoxymethylbenzyl 3-(2-methyl-1-propenyl)-2,2-dimethylcyclopropanecarboxylate, 2-methyl-4-oxo-3-(2-propynyl)-cyclopent-2-enyl 3-(2,2-dichlorovinyl)-2,2-dimethylcyclopropanecarboxylate, 2,3,5,6-tetrafluoro-4-methoxymethylbenzyl 3-(1-propenyl)-2,2, dimethylcyclopropanecarboxylate, 2-methyl-3-allyl-4-oxo-2-cyclopenten-1-yl 2,2,3,3-tetramethylcyclopropane carboxylate, and natural pyrethrin. Those compounds may be used solely, or more than two of those compounds may be mixed to be used.

Moreover, in view of pest control activity and volatility, it is preferable to use a compound in the pyrethroid group selected from the following compounds such as: 2,3,5,6-tetrafluoro-4-methoxymethylbenzyl 3-(1-propenyl)-2,2-dimethylcyclopropanecarboxylate, 2,3,5,6-tetrafluoro-4-methylbenzyl 3-(1-propenyl)-2,2-dimethylcyclopropane carboxylate, and 2,3,5,6-tetrafluorobenzyl 3-(2,2-dichloroethenyl)-2,2-dimethylcyclopropanecarboxylate. Further, in view of pest control activity and volatility, it is more preferable to use a compound in the pyrethroid group selected from the following compounds such as: 2,3,5,6-tetrafluoro-4-methoxymethylbenzyl 3-(1-propenyl)-2,2-dimethylcyclopropanecarboxylate, and 2,3,5,6-tetrafluoro-4-methylbenzyl 3-(1-propenyl)-2,2-dimethylcyclopropane carboxylate.

The above-mentioned compounds, namely 2,3,5,6-tetrafluoro-4-methoxymethylbenzyl 3-(1 -propenyl)-2,2-dimethylcyclopropanecarboxylate and 2,3,5,6-teterafluoro-4-methylbenzyl 3-(1 -propenyl)-2,2-dimethylcyclopropane carboxylate, are described in Japanese Un-examined Patent Publication, Tokukai, No. 2000-63329 (published on Feb. 29, 2000), as pest control active compounds, and can be manufactured in accordance with a method described in the Patent Publication.

As a method of holding the pest control component in the pest control component holder 45, it is possible to employ various methods. Besides methods of absorbing, coating, printing, or kneading on the pest control component holding material 45a the pest control component or a composition in which the pest control component is included with solvent, pigment, antioxidant, synergist, absorbent material of ultraviolet rays, anti-light stabilizer, or the like, it is possible to employ a method of solidifying and molding the pest control component or the composition including the pest control component.

An amount of the pest control component to be held in the pest control component holder 45 is dependent on for what purpose it is used, in which kind of surroundings it is used, and for how long it is used. Generally, the amount of the pest control component to be held in the pest control component holder 45 is in a range between 0.001 g and 10 g, preferably in a range between 0.001 g and 5 g, more preferably in a range between 0.1 g and 1 g.

Moreover, as discussed above, the liquid holder 46 may have any arrangement, provided that the liquid holder 46 is able to hold the liquid 5, which is supplied from the indicator 2 to the liquid holder 46, so that the liquid 5 is volatilized into the air. It is preferable that the liquid holder 46 can absorb the liquid 5 that is supplied from the indicator 2 to the liquid holder 46, so that the end point can be easily controlled and the operation of the pest control device can be interrupted. Further, it is also a preferable arrangement for the liquid holder 46 that the liquid 5 held in the liquid holder 46 is appropriately volatilized by an air stream passing through the liquid holder 46.

For this reason, the liquid holding material 46a used in the liquid holder 46 is preferred to be able to absorb the liquid 5, which is supplied from the indicator 2 to the liquid holder 46, and to appropriately volatilize the liquid 5 held in the liquid holding material 46a by the air stream passing through the liquid holding material 46a.

Specific examples of the liquid holding material 46a used in the liquid holder 46 are: felt, cotton, cloth, pulp, paper, a porous resin (polypropylene foam, urethan foam, and the like), un-woven fabric, asbestos, porous ceramics, synthetic fiber (nylon, polyester, polypropylene, polyethylene, and the like), natural fiber (wool, silk, cotton, hump, and the like), inorganic fiber (glass fiber and the like), inorganic moldings, and products of those materials. However, the liquid holding material 46a of the prevent invention is not limited to those raw materials.

It is preferred that the liquid holding material 46a has a large surface area with respect to volume, to constitute the liquid volatilization surface 46b. Moreover, it is also preferred that the liquid holding material 46a has a large gas permeability. For this reason, it is preferred to use, for example, a material having a net-shaped or a honeycomb-shaped material for the liquid holding material 46a. Further, it is also possible to expand the surface area of the liquid holding material 46a with respect to volume, by laminating, by folding or by partially jointing the net-like or the honeycomb-like shaped materials, if necessary.

Moreover, the liquid holder 46 is provided with a projected section 46d, which is extended into the indicator 2. The liquid holding material 46a is so provided as to form the projected section 46d. The liquid holder 46, shown in FIGS. 3 and 4(a), has such a constitution that the liquid holding material 46a is extended to the projected section 46d, in accordance with shapes of the upper frame 43 and the lower frame 44 as the volatile substance holding fixing section. In case the liquid holder 46 is provided with the projected section 46d in this way, the volatile substance material holder 47 may have a supporting section to support the projected section 46d, as indicated by a long dashed double-short dashed line in FIG. 4(b). Note that, needless to say, the supporting section has such a constitution that does not retard the supply of the liquid 5 into the liquid holding material 46a by the projected section 46d.

Moreover, as shown in FIGS. 1 and 2, the indicator 2 is provided with (a) a bottle 3 (liquid containing means, liquid container) for containing the liquid 5 to be supplied to the liquid holder 46 in the volatile substance holder 40, and (b) a wick 4 as liquid supplying means (liquid supplying system) for supplying the liquid 5, which is contained in the bottle 3, to the liquid holder 46.

In the indicator 2, the wick 4 is suspended inside the bottle 3 in such a manner that a part of the wick 4 is stuck out from a opening section 3a, which is disposed in an upper part of the bottle 3, so that the wick 4 touches the liquid holding material 46a in the projected section 46d of the liquid holder 46. In this way, the liquid 5 contained in the bottle 3 is continuously supplied into the volatile substance holder 40 via the wick 4, so that an amount of the liquid 5 left in the bottle 3 indicates a remaining amount of the pest control component (active component) held by the pest control component holder 45 in the volatile substance holder 40 located in the chamber 20 of the pest control device main body 1.

Mainly a combination of those conditions is set (or decided) in accordance with at least one of (a) a combination of the pest control component and its pest control component content, and (b) a combination of the liquid 5 contained in the bottle 3 and its amount to use. Those conditions are, namely: the type of the pest control component and its pest control component content, the type of the liquid 5 contained in the bottle 3 and its amount to use, the ratio of a surface area of the pest control component volatilization surface 45b of the pest control component holder 45 over that of the liquid volatilization surface 46b of the liquid holder 46, the material of the pest control component holder 45, and the material of the liquid holder 46.

The setting is carried out by appropriately adjusting the following variable factors, for example: the type of the pest control component and its pest control component content, the type of the liquid 5 contained in the bottle 3 and its amount to use, the ratio of a surface area of the pest control component volatilization surface 45b of the pest control component holder 45 over that of the liquid volatilization surface 46b of the liquid holder 46, the material of the pest control component holder 45, and the material of the liquid holder 46.

Moreover, both of the pest control component volatilization surface 45b of the pest control component holder 45 and the liquid volatilization surface 46b of the liquid holder 46 are located inside the chamber 20 of the pest control device main body 1, and are subjected, in a same space, to an air stream generated by the same air stream generator 23. In other words, the pest control component volatilization surface 45b of the pest control component holder 45 and the liquid volatilization surface 46b of the liquid holder 46 are placed in the same environment for volatilization.

For this reason, there is an interrelationship between (a) the volatilization of the liquid 5 contained in the bottle 3, which functions as an indicator, and (b) the volatilization of the pest control component held in the pest control component holder 45 in the volatile substance holder 40. Therefore, the liquid 5 contained in the bottle 3 is supplied into the liquid holder 46 in the volatile substance holder 40 so as to make it possible to know by sight how much the pest control component is left (or reduced) in the pest control component holder 45.

The bottle 3 used in the indicator 2 is not limited to a specific container, provided that the bottle 3 has a space to contain the liquid 5, and does not leak the liquid 5 out for a certain period, for example, more than 1 year. However, it is preferable that the bottle 3 is made of a raw material that is transparent or translucent so that the user can see the amount of the liquid 5. This allows the bottle 3 to be utilized as an indicator (indicating means), thereby reducing a manufacturing cost of the pest control device, while allowing the user to easily check the amount of the liquid 5 remained in the bottle 3, and furthermore, the amount of the pest control component held in the pest control component holder 45.

Examples for such a raw material are: polyvinyl chloride, polyethylene terephthalate, polyacryl nitrile polyethylene, copolymer of vinyl chloride and vinyl acetate, a synthetic resin of a combination of those materials and glass. Meanwhile, the raw material of the bottle 3 is not limited to those raw materials.

Moreover, the bottle 3 is provided with a wick holder 6 for fixing the wick 4 and sealing the opening section 3a of the bottle 3 so as to prevent the liquid 5 in the bottle 3 from being volatilized.

The wick 4 can be made from any raw material, which can absorb the liquid 5 contained in the bottle 3, to supply the liquid 5 to the liquid volatilization surface 46b of the liquid holder 46, and the raw material is not limited to a specific material.

Specifically, examples for absorbent materials for the wick 4 are: felt, cotton, cloth, pulp, paper, a porous resin (polypropylene foam, urethan foam, and the like), un-woven fabric, asbestos, porous ceramics, synthetic fiber (nylon, polyester, polypropylene, polyethylene, and the like), natural fiber (wool, silk, cotton, hump, and the like), inorganic fiber (glass fiber and the like), inorganic moldings, and products of those materials.

Moreover, the liquid 5 used in the present invention is not limited to a specific one, provided that the liquid 5 is a liquid that is wholly or partially volatile at ordinary temperature. If the liquid 5 functions merely as the indicator, a solvent such as water, hydrocarbon, ester, alcohol or their solution may be utilized for the liquid 5.

Moreover, the liquid 5 may include, in accordance with need of a user, chemicals, for example: a pest control component identical with, or different from the pest control component, a component derived from a vegetable essential oil (such as a fragrant component, an antibacterial component, a pest-repellant component), a synthetic pest-repellant agent such as DEET, fragrance, color agent, a stabilizer such as dibutylhydroxytoluene (BHT), absorbent material of ultraviolet ray, and surfactant.

Furthermore, when the bottle 3 is made of the transparent or translucent material so as to check by sight the remaining amount of the liquid 5, the liquid 5 may include a pigment and the like, which can dissolve in the liquid 5.

When the liquid 5 includes the various component in accordance with need of a user, the indicator 2 can perform as a chemical holding section, beside as the indicator, thereby allowing a chemical to be used in combination with the pest control agent, even if the chemical may be more volatile or less volatile compared to the pest control component, or even if the chemical is a solid.

This overcomes such a problem that a chemical having a low boiling point, such as a fragrance, is wholly volatilized away before the end of efficacy of the pest control agent due to a difference in their boiling points when the chemical having the low boiling point and the pest control agent are absorbed together in a holder in advance. Thus, in the above arrangement of the present invention, the pest control component and the chemical can synchronize their end points of efficacy, easily and precisely. For this reason, the pest control device can be incorporated with various additional functions, such as deodorization, an antibacterial function, and a fragrance function, to meet needs of users. In addition, active components of those functions can have a serviceable time (a period until an end of efficacy of the active components) that is arbitrarily set.

It is effective to use a chemical, which is included in the liquid, and which is more volatile than the pest control component held in the pest control component holder 45. However, it is also possible to use a chemical (a low volatile chemical) less volatile than the pest control component held in the pest control component holder 45, when the following constitutions are appropriately changed, as discussed above: types of the pest control component and its pest control component content, the types of the liquid 5 contained in the bottle 3 and its amount to use, the ratio of a surface area of the pest control component volatilization surface 45b of the pest control component holder 45 over that of the liquid volatilization surface 46b of the liquid holder 46, the material of the pest control component holder 45, and the material of the liquid holder 46.

It is possible to set arbitrarily the amount of the liquid 5 contained in the bottle 3. But, it is preferable that the bottle 3 contains no liquid 5 or a very little amount of the liquid 5 at a time when the pest control component held in the pest control component holder 45 becomes no more effective in terms of the pest control activity, that is, at the time of the end of efficacy, or just before the end of efficacy. Of course, it is more preferable that the bottle 3 has no liquid 5 or a very little amount of the liquid 5 at the time of the end of efficacy.

When the pest control device is used, it is possible to set the volatile loss of the liquid 5 contained in the bottle 3 and the volatile loss of the pest control component to have a relationship each other. Because of this, it is easy to control the end point and volatile loss. Therefore, it is possible to set arbitrarily the disappearance point of the liquid 5 contained in the bottle 3 and the end point of efficacy of the pest control component.

Figure 6:
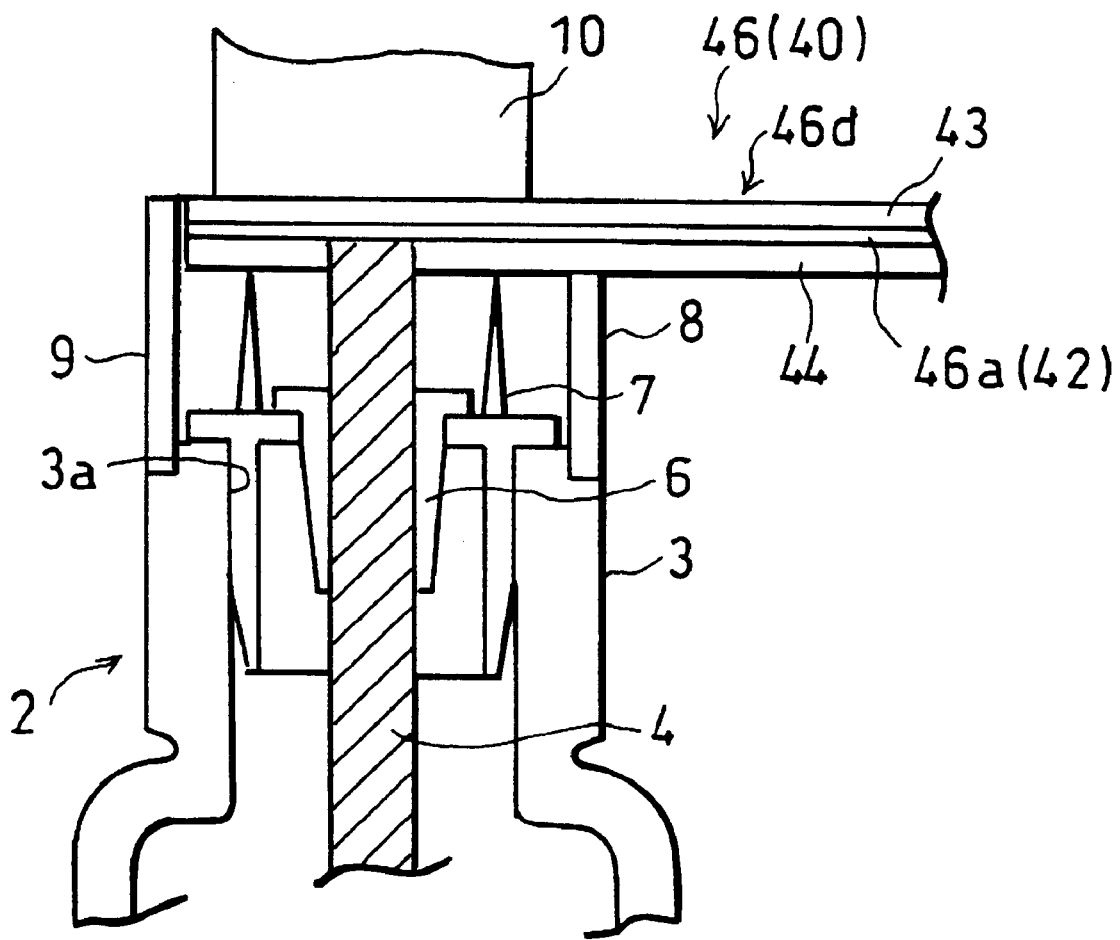
FIG. 6 is a cross-sectional view showing constitution of a touching section between the liquid holder and a wick in the pest control device.
Figure 7A:
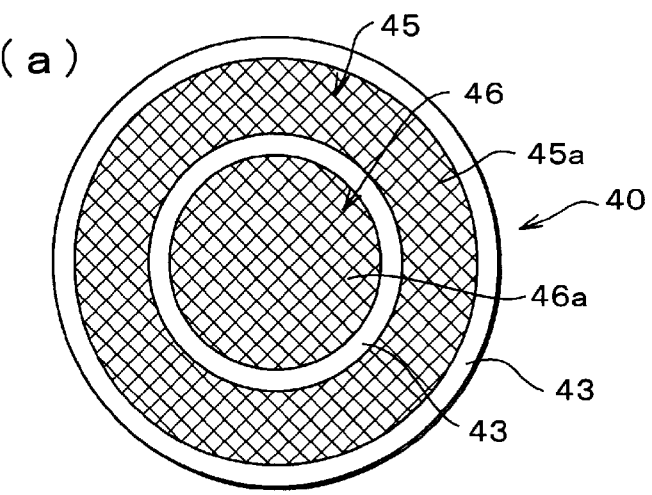
FIG. 7(a) is a plan view illustrating an example of a shape of the volatile substance holder of the pest control device.
Figure 7B:
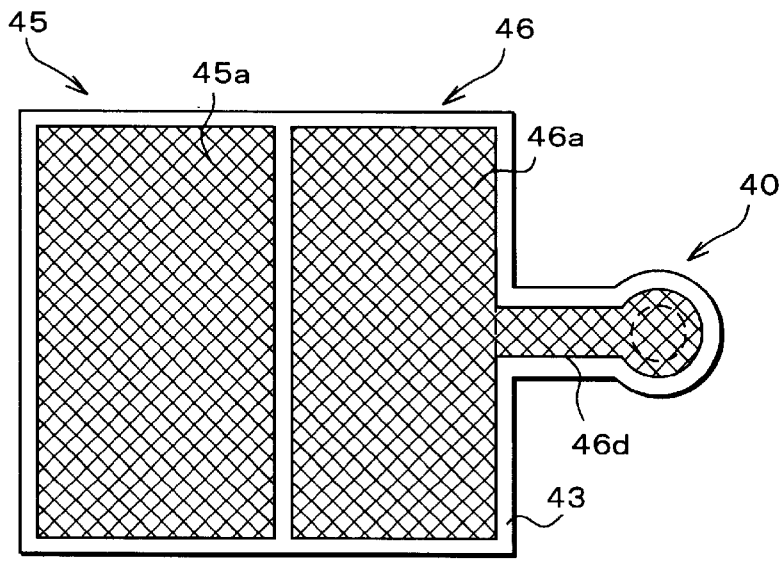
FIG. 7(b) is a plan view showing another example of a shape of the volatile substance holder of the pest control device.
Figure 7C:
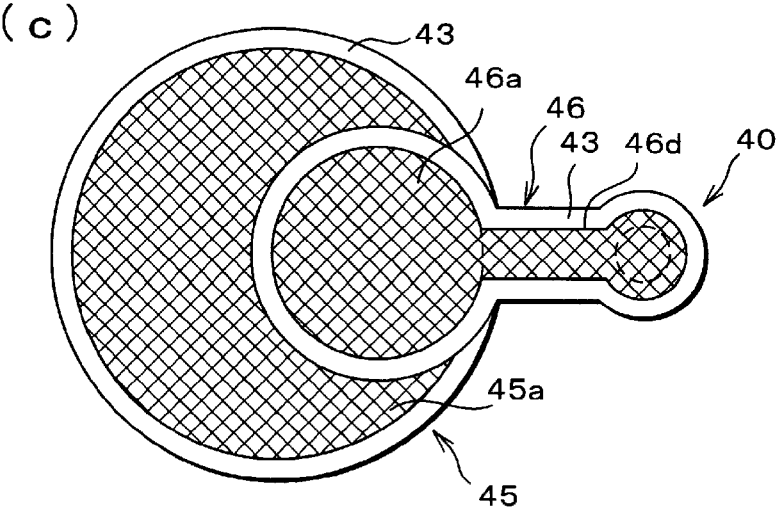
FIG. 7(c) is a plan view showing still another example of a shape of the volatile substance holder of the pest control device.

The liquid 5 absorbed into the wick 4 is supplied into the liquid volatilization surface 46b of the liquid holder 46 via the wick 4 that touches the liquid holding material 46a of the projected section 46d of the liquid holder 46, as shown in FIGS. 2, 3 and 6.

In this case, when the wick 4 is made of a soft material, it is preferable that a rib 7 (peaking section) is formed, as shown in FIG. 6, around the wick 4, for example, in the wick holder 6. The rib 7, as a stopper system for the wick 4, pushes the wick 4 appropriately into the liquid holding material 46a without twisting the wick 4, while the rib 7 is made to touch the lower frame 44 of the liquid holder 46 so as to support the liquid holder 46. The bottle 3 is provided with a supporting wall 8 and a fixing wall 9. The supporting wall 8 leads liquid holder 46 to a section (a touching section) where the liquid holder 46 is touched by the wick 4, while supporting the liquid holder 46 so that the wick 4 touches the liquid holding material 46*a*. The fixing wall 9, as a stopper system, supports the liquid holder 46 in a fixed position.

Moreover, in case the wick 4 touches the liquid holding material 46*a*, a pressing rubber 10 is provided on the touching section where the liquid holding material 46*a* of the liquid holder 46 is touched by the wick 4, so as to fix the touching section in a certain position.

Note that, the method for fixing the touching section in the certain position is not limited to the provision of the pressing rubber 10 on the touching section.

Moreover, while the pest control device shown in FIG. 2 is provided with the bottle 3 in a position next to the pest control device main body 1, so as to make a liquid in the bottle 3 touch the projected section 46*d* provided in the liquid holder 46, so as to supply the liquid in the bottle 3 to the liquid volatilization surface 46*b* of the liquid holder 46. However, the method of supplying the liquid in the bottle 3 is not limited to this. For example, as shown in FIG. 7(*a*), the liquid holder 46 can be provided at a center of the volatile substance holder 40, so that the bottle 3 is disposed on a reverse side of the liquid holder 46 so as to let the wick 4 touch a reverse side of the liquid holding material 46*a* of the liquid holder 46. When the bottle 3 is disposed in the position next to the pest control device main body 1, the height of the pest control device may be limited. On the other hand, when the bottle 3 is disposed on the reverse side of the liquid holder 46, the pest control device has a smaller width to be slim. The bottle 3 may be appropriately positioned in accordance with the usage and the using environment, and its position is not limited specifically.

Figure 4:
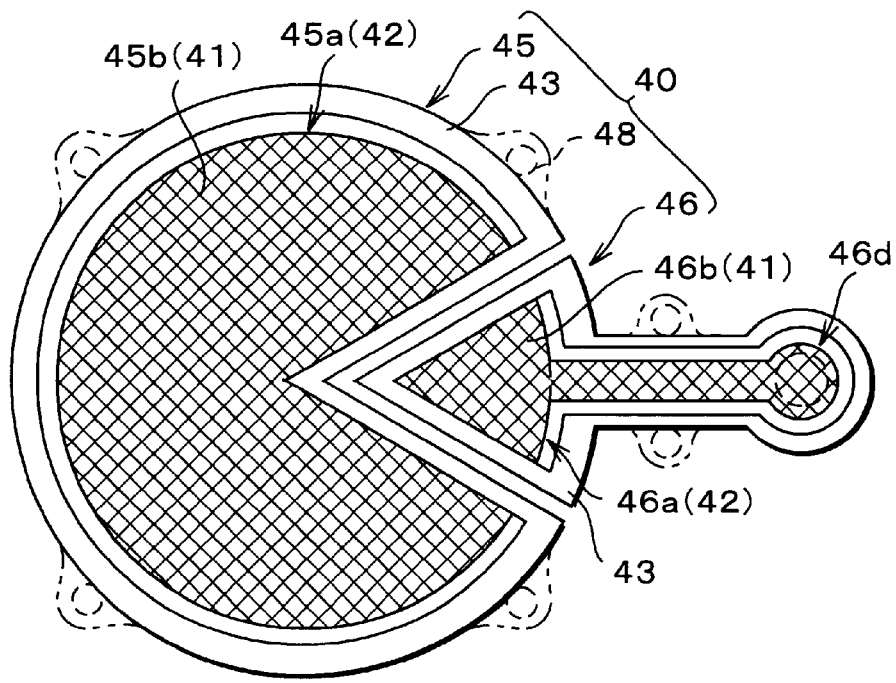
FIG. 4(a) is a plan view showing constitution of a pest control component holder and a liquid holder of the pest control device.
FIG. 4(b) is a plan view illustrating constitution of a supporting frame for the volatile substance holder, which supports the pest control component holder and the liquid holder shown in FIG. 4(a).
Figure 4:
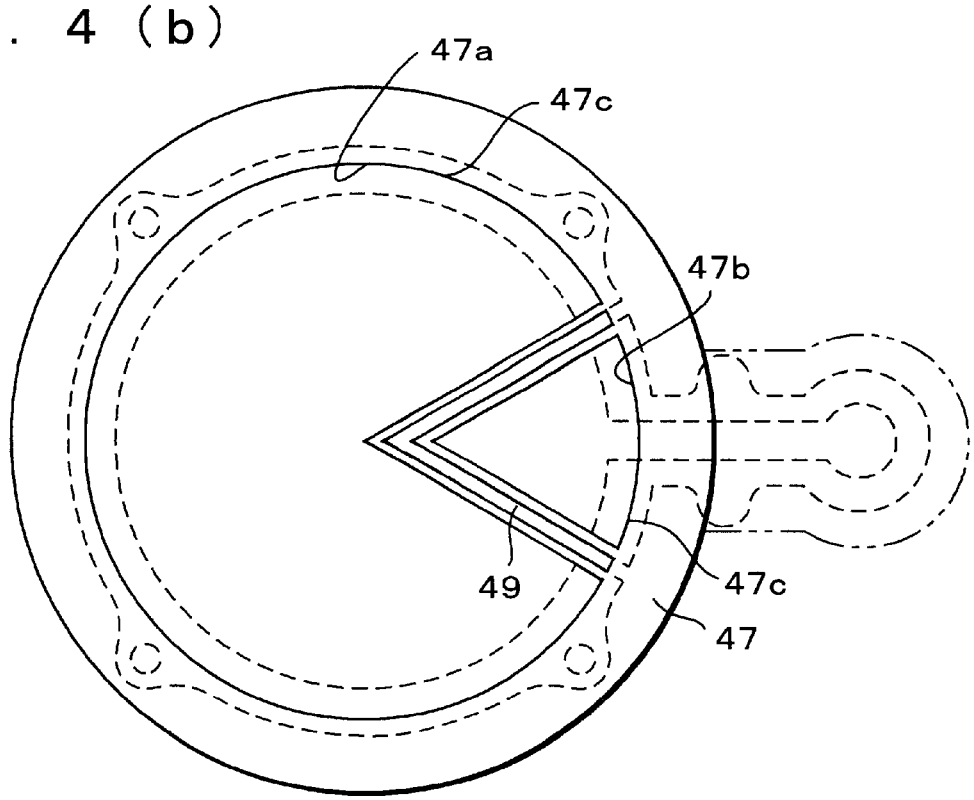

Moreover, the volatile substance holder 40 is not limited to a certain shape. Thus, the volatile substance holder 40 may have a circular shape, as shown in FIG. 4(*a*), and FIG. 7(*a*), or a quadrangular shape as shown in FIG. 7(*b*). In addition, the liquid holder 46 of the volatile substance holder 40 is also not limited to a certain shape. Thus, the liquid holder 46 may have a triangle shape as shown in FIG. 4(*a*), a quadrangular shape as shown in FIG. 7(*b*), or a circular shape as shown in FIGS. 7(*a*) and 7(*c*). Further, the projected section 46*d* may be located in any position as long as the projected section 46*d* is positioned in accordance with the position of the bottle 3. The liquid holder 46 in the volatile substance holder 40 may also be placed in accordance with the position of the bottle 3. Thus, the liquid holder 46 may be provided on an edge of the volatile substance holder 40, as shown in FIGS. 4(*a*), 7(*b*) and 7(*c*), or at a center of the volatile substance holder 40, as shown in FIG. 7(*a*). Therefore, there is no specific limitation in a shape and a position of the volatile substance holder 40, the pest control component holder 45 and the liquid holder 46. Moreover, in FIGS. 4(*a*), 5, 7(*b*) and 7(*c*), it is arranged that the touching section of the projected section 46*d*, where the wick 4 touches the projected section 46*d*, has a bulged shape, but the projected section 46*d* need not have such a bulge-shaped touching section to be touched by the wick 4.

Furthermore, as a liquid supplying system (liquid supplying means) for supplying the liquid 5 to the liquid holding material 46*a*, most suitably used is a liquid absorbing supplying system, in which used as the wick 4 is an absorbent material to absorb the liquid in the bottle 3, because such a liquid absorbing supplying system can supply the liquid to the liquid holder 46 with ease, at a low cost, and continuously at a constant rate. However, the liquid supplying system is not limited to this, and any system, which can supply the liquid 5 contained in the bottle 3 to the liquid volatilization surface 46*b* of the liquid holder 46, may be employed as the liquid supplying system.

Figure 8A:
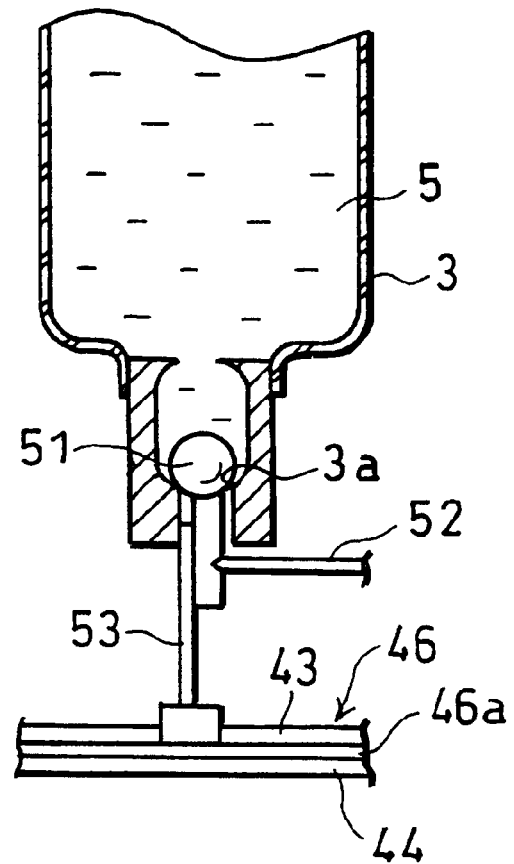
FIGS. 8(a) and 8(b) are explanatory views illustrating operation of another liquid supplying means of the pest control device.
Figure 8B:
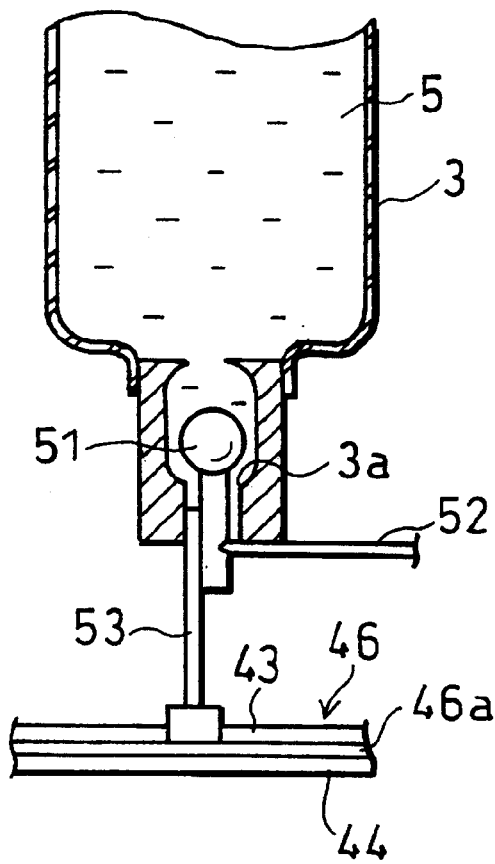

For example, it may be arranged as shown FIGS. 8(*a*) and 8(*b*), where (a) the bottle 3 is supported in such a manner that the opening section 3*a* is at a bottom of the bottle 3, (b) the liquid supplying system is disposed in the bottle 3 so that the liquid supplying system is movable, for example, in accordance with application of pressure, (c) provided are a ball 51, a sealer moving section 52, and an absorbent material 53. The ball 51 seals, as a sealer, the opening section 3*a* of the bottle 3, while the sealer moving section 52 pushes up the ball 51 to open the opening section 3*a* of the bottle 3, so that the absorbent material 53 absorbs the liquid 5 discharged from the opening section 3*a* that is opened by the sealer moving section 52, so as to supply the liquid 5 to the liquid holding material 46*a*.

In this case, as shown in FIG. 8(*a*), the ball 51 seals the opening section 3*a* when no electric source is supplied. As shown in FIG. 8(*b*), the ball 51, which has been sealing the opening section 3*a*, is pushed up by the sealer moving section 52 that is operated when an electric source is supplied. As a result, the pushing up the ball 51 makes a gap between the opening section 3*a* and the ball 51, so as to flow the liquid 5 out via the gap by gravity. The liquid 5 flown out of the gap is gathered by the absorbent material 53 that touches the liquid holding material 46*a*. In this manner, the liquid 5 contained in the bottle 3 is supplied to the liquid holding material 46*a*. In this case, if the air stream generator 23 is required for volatilizing the liquid 5 and the pest control component, the sealer moving section 52 and the air stream generator 23 are operated in a synchronizing manner (for example, at the same time) when the electric source is supplied. Note that, the sealer for closing the opening section 3*a* is not limited to the ball 51. For example, it may be arranged that the sealer moving section 52 is operated to open and close a valve.

Figure 9:
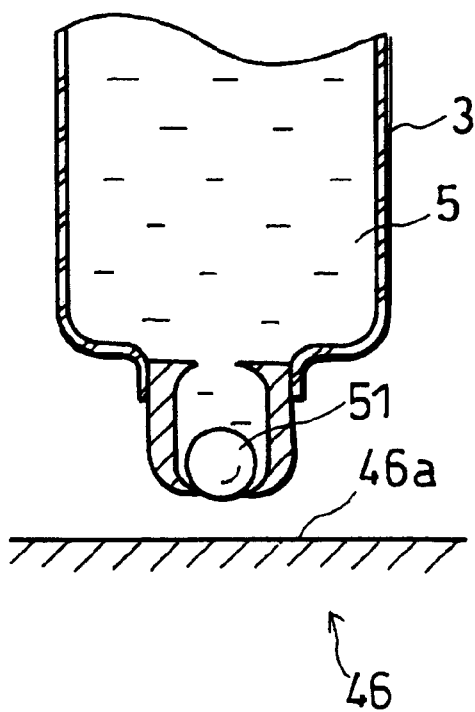
FIGS. 9(a) and 9(b) are explanatory views illustrating operation of still another liquid supplying means of the pest control device.
Figure 9:
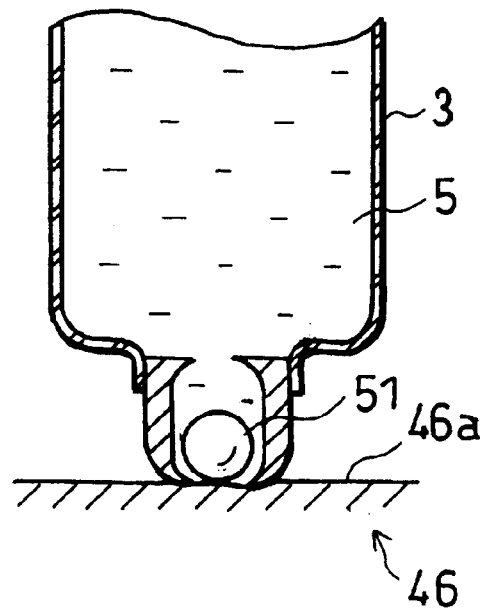

Moreover, the liquid supplying system (liquid supplying means), which supplies the liquid 5 to the liquid holding material 46*a*, may have such an arrangement, for example as shown in FIGS. 9(*a*) and 9(*b*), that (a) the bottle 3 is supported in such a manner that the opening section 3*a* is at a bottom of the bottle 3, (b) the liquid supplying system is disposed in the bottle 3 so that the liquid supplying system is movable, for example, in accordance with application of pressure, (c) provided are a ball 51, and a liquid container moving section (not shown). The ball 51, as a sealer, seals the opening section 3*a* of the bottle 3. The liquid container moving section supports the bottle 3 in such a manner that the opening section 3*a* is at the bottom of the bottle 3, and the ball 51 is pressed onto the liquid holding material 46*a* when the bottle 3 is lowered down.

In this case, the liquid 5 contained in the bottle 3 is supplied to the liquid holding material 46*a* in the following manner. As shown in FIG. 9(*a*), where no electric source is supplied, the ball 51 seals the opening section 3*a*. When an electric source is supplied, as shown in FIG. 9(*b*), the liquid container moving section is driven to move the bottle 3 so as to press a tip of the ball 51 onto the liquid holding material 46*a*. As a result, the ball 51 is slightly pushed up so as to make a gap between the ball 51 and the opening section 3*a*. The liquid 5 contained in the bottle 3 flows out through the gap, so as to supply the liquid 5 in the bottle 3 to the liquid holding material 46*a*. Note that, again in this case, if the air stream generator 23 is required to volatilize the liquid 5 and the pest control component, the liquid container moving section and the air stream generator 23 are driven in a synchronizing manner when the electric source is supplied.

Moreover, as the method for checking how much liquid 5 is left in the bottle 3, it is the easiest and cheapest method that the bottle 3 is made of a transparent or translucent raw material, so as to let a user check by sight how much the liquid 5 is left in the bottle 3. Besides this method, for example, other methods for checking may be used, as shown in FIGS. 10(a) and 10(b), where the bottle 3 is provided, as an electric kettle, with a container 61, which is opaque, a pipe 62 (an indicator), which is transparent or translucent, and formed along the container 61 and is connected to a bottom of the container 61. In this arrangement, it is possible to check by sight how much the liquid 5 is left in the pipe 62 when the pipe 62 is viewed in front, thereby checking by sight how much liquid 5 is left in bottle 3.

Note that, as the liquid supplying means for supplying the liquid 5 contained in the bottle 3 to the liquid holder 46, it is possible to have, for example, such an arrangement where the above-discussed wick 4 is used and suspended in the container 61 so that a part of the wick 4 is stuck out from an opening section (not shown) that is formed on a top of the container 61, so as to allow the wick 4 to touch the liquid holding material 46a. As another possible arrangement, a pump (not shown) may be used to supply the liquid 5 continuously from the container 61 to the liquid holding material 46a.

Furthermore, as still another method, for example, it is possible to employ such an arrangement where measuring-displaying apparatus (indicating means) (not shown) such as a meter used in an automobile to indicate how much gasoline is left, is used so as to measure how much liquid 5 is left in the bottle 3, and to indicate a result of the measurement by using a meter. With this arrangement, it is also possible to check by sight how much the liquid 5 is left in the bottle 3.

Furthermore, it is also possible to have such a detecting-displaying arrangement in which a sensor (not shown) is provided in the bottle 3 so that the sensor, which is soaked in the liquid 5, is exposed in accordance with the reduction of the liquid 5 in the bottle 3, so that the exposure changes electric conductivity of the sensor so as to turn on a lamp. The lamp may be a single lamp, a series of lamps to indicate the reduction in a stepwise manner, or a flashing lamp.

As the indicating means, a most suitable method may be adapted in accordance with components of the liquid 5, or other conditions.

Figure 11:
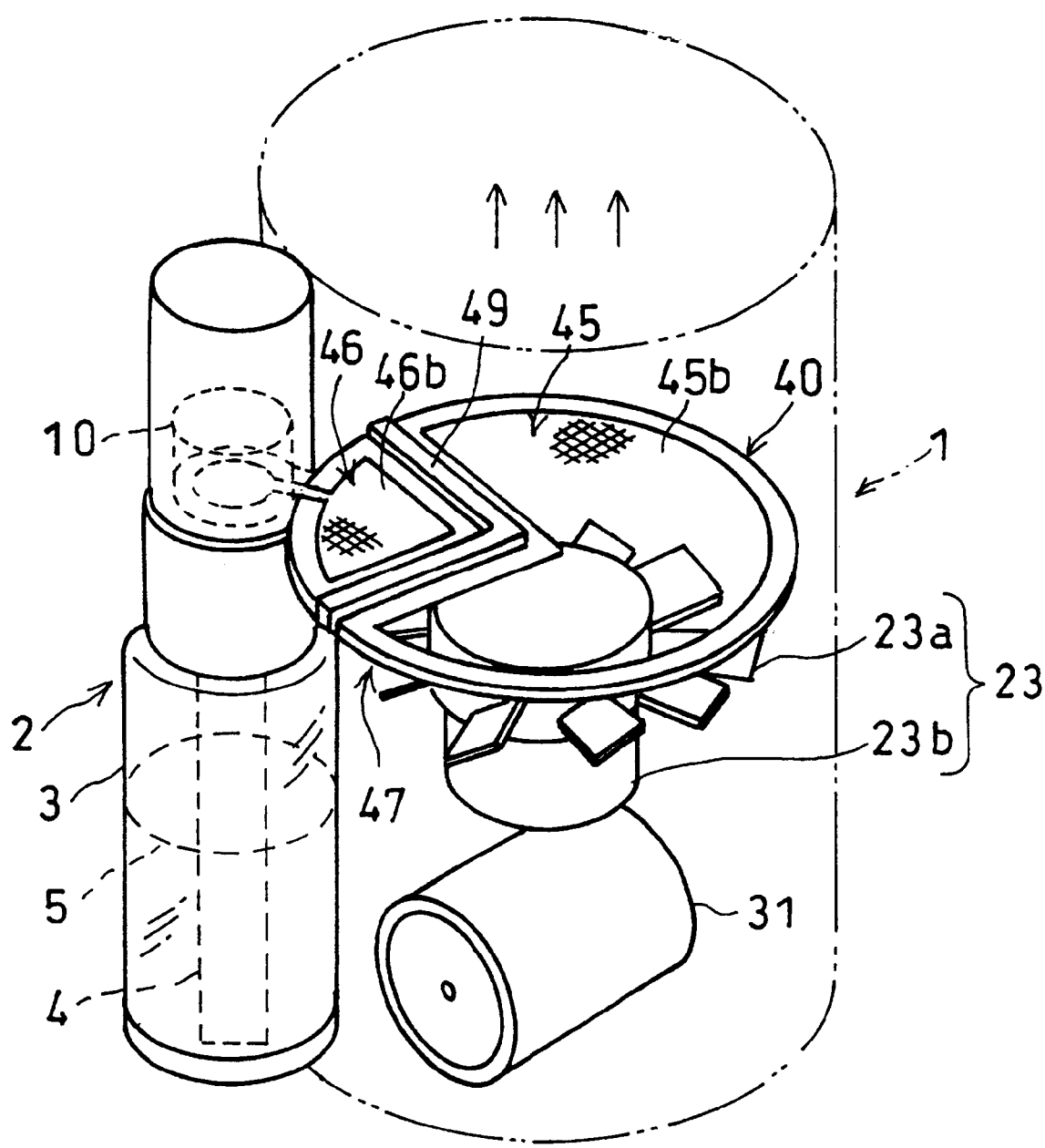
FIG. 11 is an explanatory view illustrating another positional arrangement of an air stream generator of the pest control device.

Moreover, in the pest control device shown in FIG. 2, the volatile substance holder 40 is placed in a position on an air exit side of the air stream generator 23, that is, on a side where the vent hole 11a is formed as the air exit hale in the pest control device main body 1. However, the volatile substance holder 40 and the air stream generator 23 are not limited to this positional arrangement, but may have such a positional arrangement, as shown in FIG. 11, in which the volatile substance holder 40 is positioned on an air intake side of the air stream generator 23, so as to send air toward the volatile substance holder 40, so as to blow the air onto the volatile substance holder 40 and to pass the air through the volatile substance holder 40.

Figure 12:
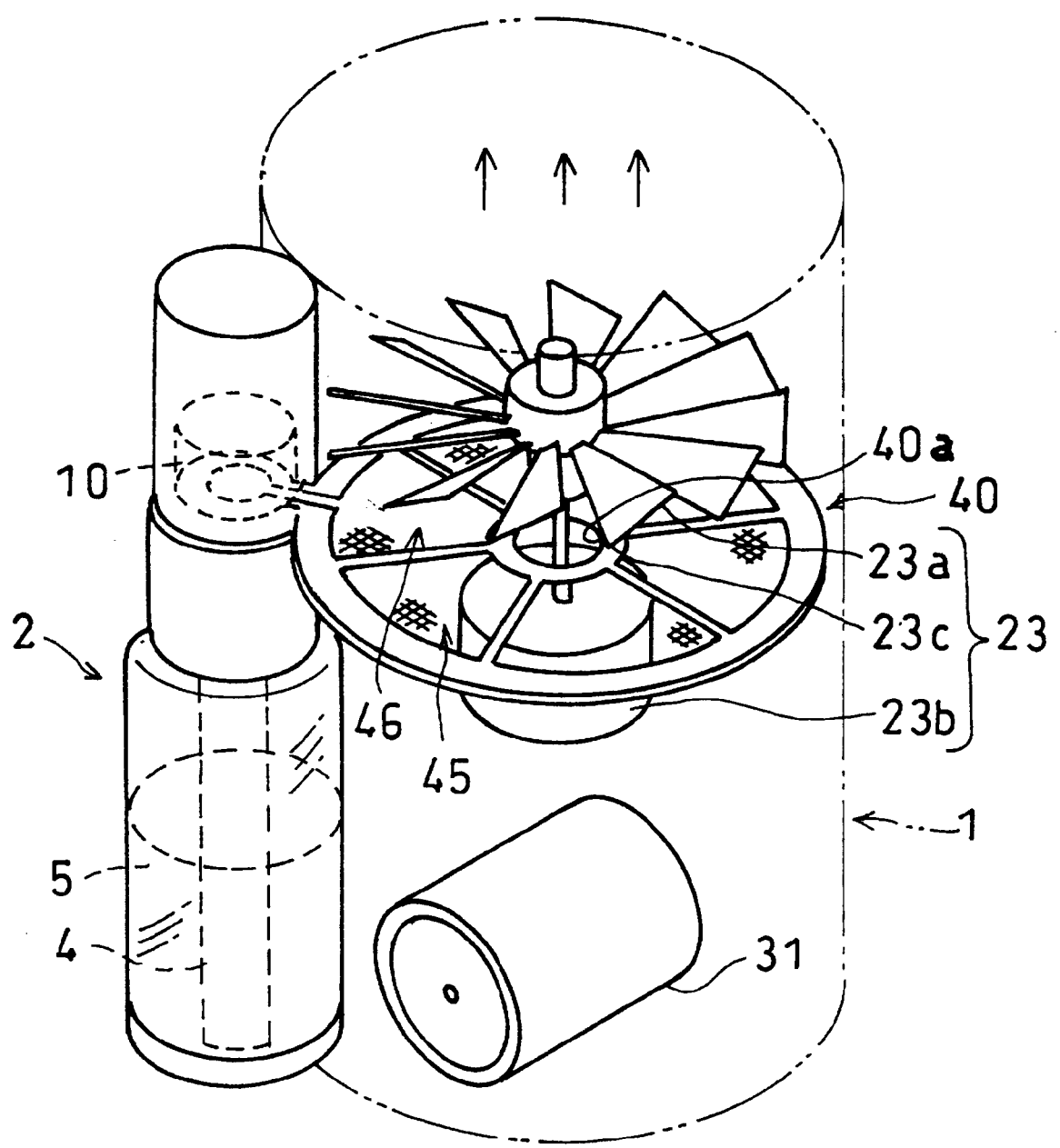
FIG. 12 is an explanatory view illustrating still another positional arrangement of an air stream generator of the pest control device.

Moreover, as shown in FIG. 12, only the air fan 23a may be disposed on the air exit side of the air stream generator 23, while the motor 23b may be placed on the air intake side of the air stream generator 23, with respect to the volatile substance holder 40. On the contrary, even though no figure is provided, only the air fan 23a may be placed on the air intake side of the air stream generator 23, while the motor 23b may be disposed on the air exit side of the air stream generator 23, with respect to the volatile substance holder 40.

In other words, the air stream generator 23 may have the following positional arrangements, with respect to the volatile substance holder 40: (a) both the air fan 23a and the motor 23b are placed on the air exit side of the air stream generator 23, (b) only the air fan 23a is positioned on the air exit side of the air stream generator 23, while the motor 23b is placed on the air intake side of the air stream generator 23, (c) both the air fan 23a and motor 23b are disposed on the air intake side of the air stream generator 23, (d) only the air fan 23a is positioned on the air intake side of the air stream generator 23, while the motor 23b is placed on the air exit side of the air stream generator 23. In the arrangements (a) and (b), the volatile component, which is volatilized from the volatile substance holder 40, is inhaled and exhausted by the air stream generator 23, while a wind is blown onto the volatile substance holder 40 to exhaust the volatile component volatilized from the volatile substance holder 40, in the arrangements (c) and (d).

Considering an efficiency of volatilizing the volatile substances held in the volatile substance holder 40, that is, the pest control component and the liquid 5, it is more preferable to have the arrangements (a) or (b), where the volatile component, which is volatilized from the volatile substance holder 40, is inhaled and exhausted by the air stream generator 23.

When the air fan 23a and the motor 23b are so disposed to sandwich the volatile substance holder 40, the volatile substance holder 40 may have, for example, a shape shown in FIG. 12 in which the volatile substance holder 40 has a through hole 40a at its center so that the supporting shaft 23c is positioned through the through hole 40a, and the air fan 23a is inserted on a top of the volatile substance holder 40. Moreover, the volatile substance holder 40 may have such a shape that the volatile substance holder 40 has a slit (not shown) so that the supporting shaft 23 can be inserted into the slit. It is possible to place the volatile substance holder 40 in an arbitrary position by interlocking the shaft 23c through the through hole 40a, or by engaging the volatile substance holder 40 with the supporting shaft 23c.

Moreover, as shown in FIG. 12, the volatile substance holder 40 is provided with a plurality of regions in a radial manner. It may be arranged that some of the plural regions, which are arbitrarily chosen, are used as a pest control component holding section (the pest control component holder 45), while the other of the plural regions, which are also arbitrarily chosen, are used as a liquid holding section (the liquid holder 46).

In the present embodiment, the air stream generated by the air stream generator 23, that is, the air stream passing through the volatile substance holder 40, may be at any speed, provided that the air stream can volatilize a sufficient amount of the pest control component held in the pest control component holder 45 when the air stream is at the speed, so that the pest control component is effective. Usually, the speed of the air stream is in a range from 0.01 m/s and 10 m/s, preferably in a range from 0.1 m/s and 10 m/s, even though the speed of the air stream should be decided depending on types of pest control components.

It is possible to appropriately control how much the pest control component and the liquid 5 are volatilized, by choosing the following factors, namely: types of the pest control component and the liquid 5, the area and material of the pest control component volatilization surface 45b in the pest control component holder 45 (that is, the material of the pest control component holding material 45a), the area and material of the liquid volatilization surface 46b in the liquid holder 46 (that is, the material of the liquid holder controlling material 46a), and an air quantity of the air stream generator 23.

Moreover, the examples shown in FIGS. 2 to 5, 7(a) to 7(c), 11 and 12, are arrangements in which the pest control component holder 45 and the liquid holder 46 are arranged on a same plane. However, the volatile substance holder 40 in accordance with the present embodiment is only requested to be able to have two types of the volatilization surfaces, one of the volatilization surfaces being able to hold the pest control component, while the other volatilization surface being able to hold the liquid 5. In short, the volatile substance holder 40 may have such an arrangement shown in FIG. 13, in which a pest control component holder 45 and a liquid holder 46 are disposed separately so that one of them are above the other.

In this case, when the liquid holder 46 is disposed in a leeward position, the pest control component held in the pest control component holder 45 is retarded from being volatilized and exhausted out of a chamber 20 to the exterior environment. Therefore, it is preferable that the liquid holder 46 is located in a windward position, that is, a position on a side of an air stream generator 23, while the pest control component holder 45 is disposed in a leeward position, that is, a position on a side of a vent hole 11a as the air exit hole.

Figure 13:
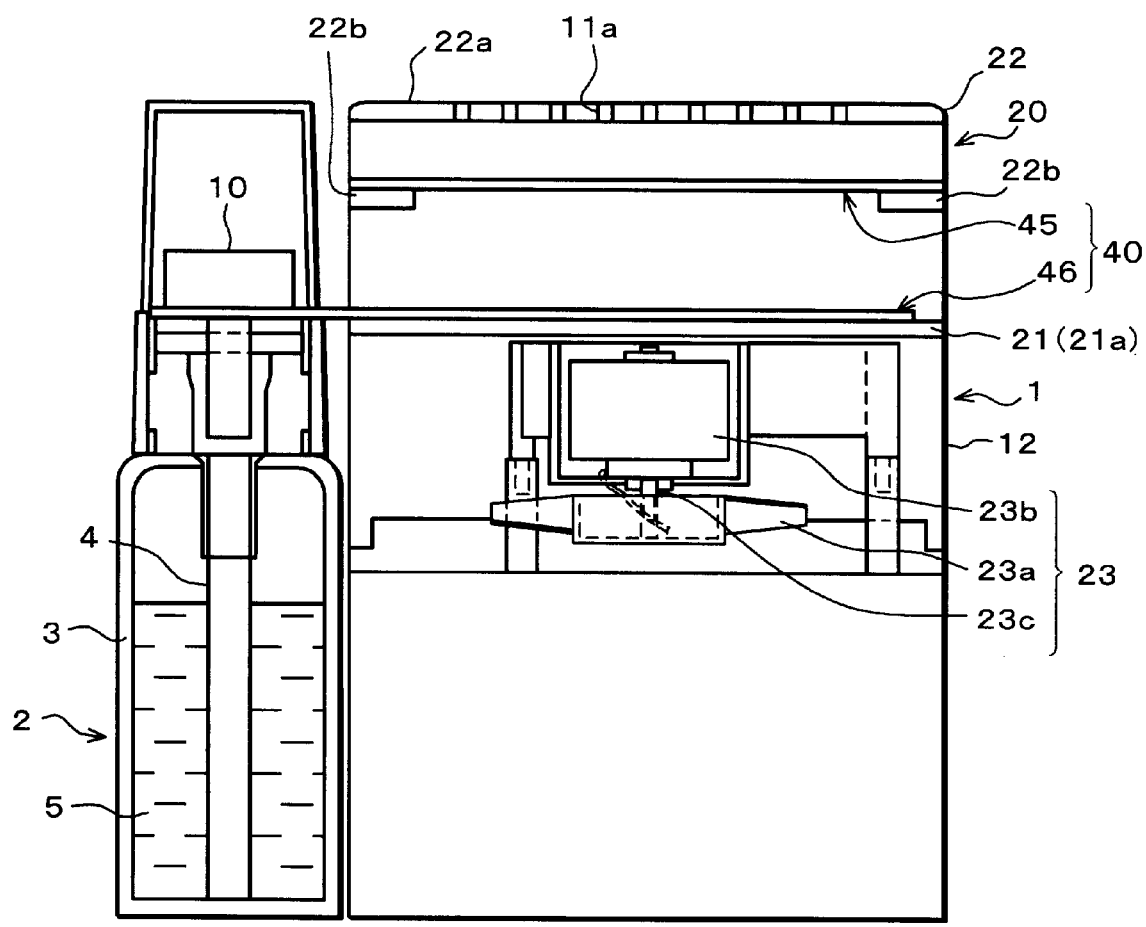
FIG. 13 is an explanatory view showing another positional arrangement of the pest control component holder and the liquid holder of the pest control device.

In FIG. 13, the pest control device has such an arrangement in which the liquid holder 46 is disposed on a top of a projected platform 21a of a pedestal 21, while the pest control component holder 45 is located on a supporting frame 22b provided on a lid 22, so that the liquid holder 46 and the pest control component holder 45 are independently and respectively disposed. However, supporting systems of the pest control component holder 45 and the liquid holder 46 are not limited to the above arrangement. For example, it is also possible to arrange that the liquid holder 46 and the pest control component holder 45 are supported by using a supporting system, such as a column, so that the liquid holder 46 and the pest control component holder 45 are connected (integrated) in such a manner that the volatilization surfaces of which, that is, the liquid volatilization surface 46b and pest control component volatilization surface 45b, are not allowed to touch each other.

Figure 14:
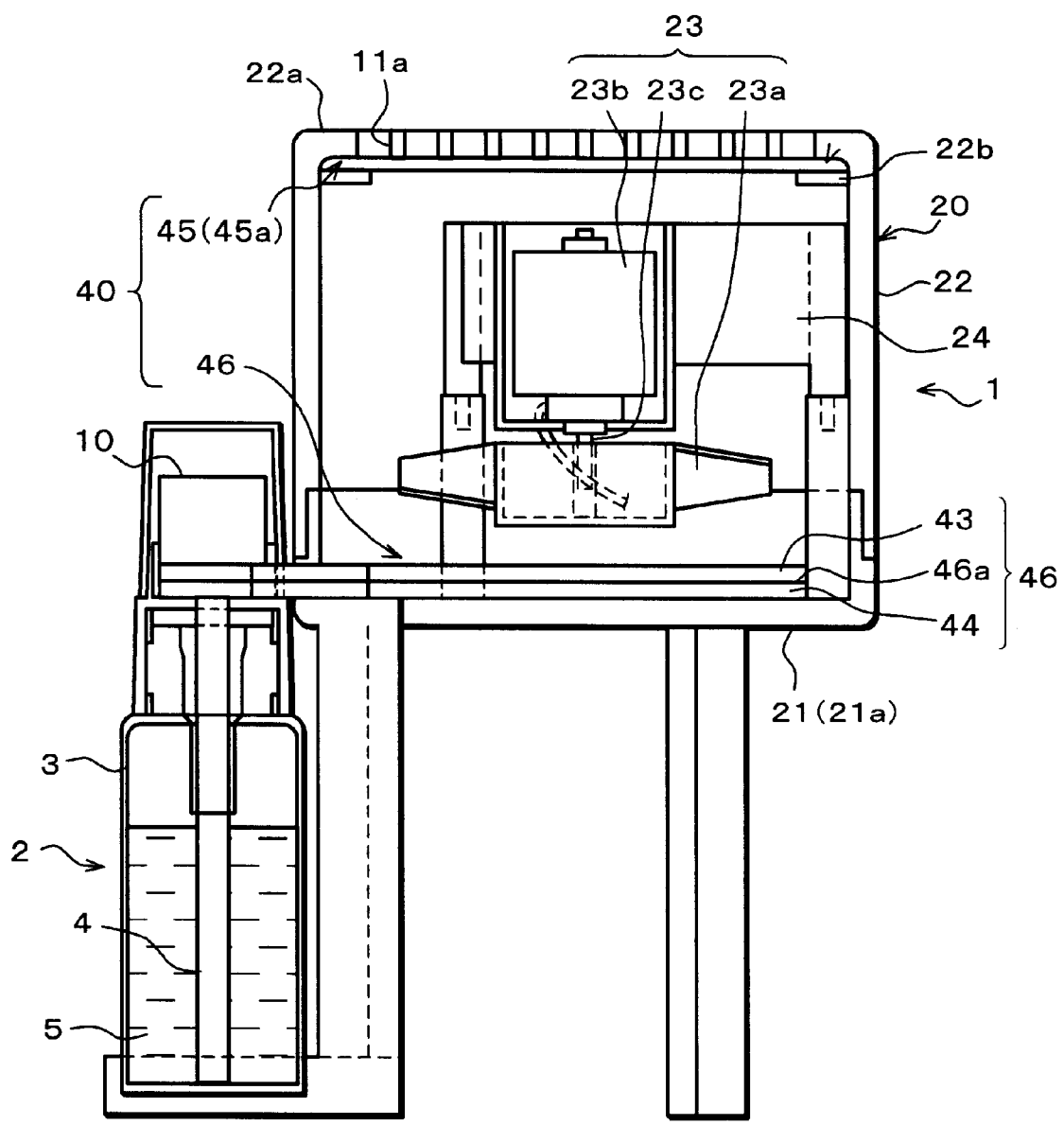
FIG. 14 is an explanatory view showing still another positional arrangement of the pest control component holder and the liquid holder of the pest control device.

Moreover, if the pest control component holder 45 and the liquid holder 46 are disposed separately from each other, it is also possible to arrange the air stream generator 23 between the pest control component holder 45 and the liquid holder 46, as shown in FIG. 14.

In this case, again, the pest control component holder 45 and the liquid holder 46 receive the air stream from the air stream generator 23 at a same timing, thereby having an interrelationship between each other. For this reason, in this case, again, it is possible to control the end points (vanishing points) of the pest control component and the liquid 5, via adjusting the various conditions discussed above. Therefore, it is also possible to check, via checking by sight how much the liquid 5 is left, how much the pest control component held the pest control component holder 45 is left (or reduced).

Furthermore, in the FIGS. 2 and 11 to 14, shown are arrangements where the pest control component holder 45 and the liquid holder 46 are disposed in the same chamber 20, in which the air stream generator 23 is provided so as to generate the air stream inside the chamber 20. However, the present invention is not limited to the arrangements, and may have such an arrangement that the pest control component holder 45 and the liquid holder 46 may be disposed respectively in separate chambers, and the pest control component holder 45 and the liquid holder 46 are vented at the same timing. In short, the chamber for the pest control component holder 45 and the chamber for the liquid holder 46 are respectively provided with an air stream generator, while the air stream generators are operated in a synchronizing manner. In this case, again, the pest control component holder 45 and the liquid holder 46 receive the air streams from the air stream generators 23 at the same time, thereby having the interrelationship between each other. The above arrangement provides a pest control device for long-life usage, because motors have a less load to operate the air stream generators.

However, it is preferable, for attaining a better interrelationship between the pest control component holder 45 and the liquid holder 46, that the pest control component holder 45 and the liquid holder 46 are disposed with an equidistance from the air stream generator 23, and in the same chamber 20. The pest control component holder 45 and the liquid holder 46 are more preferably disposed on a same plane, in order to attain the equidistance from the air stream generator 23. Moreover, the above arrangement is inexpensive and simple.

Moreover, in the present embodiment, for example in FIG. 2, illustrated is the arrangement in which the volatile substance holder 40 is so disposed that the volatile substance volatilization surface 41 thereof is horizontal. However, the arrangement of the volatile substance holder 40 is not limited to this. It is also possible to have such an arrangement in which the volatile substance holder 40 is disposed so that the volatile substance volatilization surface 41 is disposed parallel to the direction of the specific gravity, in other words, for example, the volatile substance volatilization surface 41 is so disposed to be parallel to the side wall 12 of the pest control device main body 1.

Moreover, the pest control component holder 45 may be supported by the inner wall of the ceiling 22a of the lid 22 and, for example, the previously-mentioned supporting frame 22b, as shown in FIG. 14. In this case, the pest control component holder 45 need not have the volatile substance holding material fixing section (the upper frame 43 and the lower frame 44). Note that, in FIG. 14, it is so arranged that only the pest control component holder 45 is provided on the lid 22, but it is also possible to arrange that the whole volatile substance holder 40 is disposed in the lid 22, for example, in the arrangement shown in FIG. 14.

Moreover, in the present embodiment, explained is the arrangement where the air stream generator 23 of the pest control device is operated by the dry battery 31. However, it is also possible to have such an arrangement that a cord is contained, instead of the dry battery 31 in a space that is used as the dry battery holding section 30 so that a commercial power source is used to operate the air stream generator 23 and the like. Note that, the use of the dry battery 31 allows the pest control device to be used without positional limitation, while miniaturizing the pest control device so as to be portable, thereby making the pest control device more convenient to use. Moreover, the dry battery holding section 30 need not be disposed below the chamber 20 as shown in FIG. 2 and the other figures, but may be disposed in an arbitral position.

Furthermore, the pest control device shown in FIG. 1 has the vent hole 11a as the air exit hole in a lattice shape, while the vent hole 11b is in a slit shape. However, the shapes of the vent holes 11a and 11b are not limited to this, and may have an arbitral shape.

Typical pests that can be controlled by the pest control device in accordance with the present embodiment are, specifically: various noxious insects and arthropods, such as mite, especially; flying insects, for example, Diptera (ex. Culex such as Culex pipiens pallens and aedine mosquito; Aedes, such as Aedes aegypti (yellow fever mosquito) and Aedes albopictus; Anopheles such as Anopheles sinensis; midge; house fly, such as muscid, Muscina stabulans (false housefly) and little housefly; blowfly; sarcophagid; banana-fly; moth flies; Tabanidae; horsefly; kaburi; Stomoxys calcitrans (stable fly).

The present embodiment, by using the above-mentioned pest control devices, is excellently effective to control the pests, while allowing the user to check by sight the reduction and the end point of the pest control component.

In addition, the pest control device may be arranged to be reusable by exchanging the volatile substance holder 40 or the volatile substance holding material 42, as the volatile substance holding means, at the end of the efficacy of the pest control component held in the volatile substance holder 40.

In this case, the volatile substance holder, the volatile substance held thereby, liquid supplying means (for example, the wick 4), the bottle 3 containing the liquid 5 and the liquid 5 are consumptive, and can be exchanged after used up, for example, if (a) a volatile substance holder in a uniform standard is used, and (b) set is each component of the liquid 5 contained in bottle 3, considering a boiling point, volatility and other characteristics of each component of the liquid 5, in accordance with (1) the type of the pest control component held in the volatile substance holder 40, and (2) the ratio of the pest control component volatilization surface 45b over the liquid volatilization surface 46b. For instance, the bottle 3 containing the liquid 5, or the liquid 5 may be exchangeable so that the user can choose arbitrarily a bottle 3 as the indicator, having a liquid including a fragrant component, for example. In this manner, it is possible to provide a pest control device and a volatile substance holder for use in the same, having various usage and method of using, while having the function of precise indication, even after those consumptive members are exchanged.

In the following, explained is an example of a method how to determine the quantity of the liquid 5 to be contained in the bottle 3. However, the method of determining the quantity of the liquid 5 is not limited to the following method.

For example, to begin with, a level of the liquid 5 (liquid level) in the bottle 3 is grasped, for example, by marking the liquid level. Next, the pest control device in accordance with the present embodiment is operated so as to carry out an experiment on pest control activity, or an experiment to determine the volatile loss per hour for the pest control component, with respect to passage of time. Then, determined is a liquid level in the bottle 3 at a time when the pest control activity, or the volatile loss per hour of the pest control component becomes lower than a target value. A consumption of the liquid 5 is calculated from a difference between the original liquid level, that is, the liquid level in the bottle 3 before the operation of the pest control device and the liquid level when the pest control activity or the volatile loss per hour of the pest control component is dropped below the target value. The consumption of the liquid 5 thus calculated is the quantity of the liquid 5 used in the experiment on the pest control activity or the experiment to determine the volatile loss per hour for the pest control component. The above method makes it possible to carry out an end point control in which the quantity of the liquid 5 contained in the bottle 3 is a variation (a variable).

Provided below is a further detailed explanation with an example on the method how to determine the quantity of the liquid 5, but the present invention is not limited to the method discussed below.

To begin with, a volatile substance holder 40 for experimental use was prepared as follows: 200 mg of 2,3,5,6-tetrafluoro-4-methoxymethylbenzyl 1R-trans-3-(1-propenyl (E/Z=1/8))-2,2-dimethylcyclopropanecarboxylate was applied and spread on evenly on a pest control component holding material 45a of a mesh made of nylon (trade mark of a synthetic polymer of polyamid type) which was supplied by Sanwa Fukuoka Co., Ltd. and having a diameter of about 5.5 cm and a thickness of about 0.2 cm. The pest control component holding material 45a is a volatile substance holder as shown in FIG. 3. Note that, the same mesh made of the nylon as the volatile substance holding material 45a was used to prepare the liquid holding material 46a. A ratio of a surface area of a pest control component holding material 45a to that of a liquid holding material 46a was 5 to 1.

Further, as a liquid 5, 15 ml of a solution, which has tetradecan and pentadecan at a ratio of 6/4, was poured in a bottle 3 (made of a glass, having a height of about 5.5 cm and a diameter of about 2.5 cm) as shown in FIGS. 1 and 2. The bottle 3 and the volatile substance holder 40 for experimental use were arranged in a pest control device main body 1 as shown in FIG. 14 so as to prepare a pest control device for experimental use. Note that, no dry battery 31 was used. Instead, a do current converted from an ac power was used.

As a wick 4, used was felt made from polyethylene and polypropyrene (having a length of 7.5 cm and a diameter of 3 mm). A fan (an air stream generator 23) of the pest control device for experimental use is operated for the experiment. In this manner, a pest control activity and a distance from a bottom of the bottle 3 to a liquid level were measured for a period of time.

The experiment for confirming of the pest control activity was carried out as follows.

To begin with, 10 of female imagines of Culex pipiens pallens were placed in a glass tube having an inner diameter of 4 cm, and a height of 12 cm, then both ends of the glass tube were sealed with nylon (trade mark; the synthetic high polymer of polyamid type) net of 16 mesh. Two of such glass tubes were prepared.

Next, a stand for the glass tubes was placed on a top of a cylinder for experimental use. The cylinder for experimental use had a height of 80 cm and a diameter of 20 cm. The stand had a width of 7.8 cm and was made of metal. The stand was so placed that the stand was across a diameter of the cylinder, passing a center of the cylinder. The stand had two holes in bilateral positions so that the two holes are respectively located in positions 4 cm distant from the center of the cylinder. The two holes had a 4 cm diameter that is identical with the inner diameter of the glass tubes. The glass tubes keeping in the female imagines of Culex pipiens pallens were placed on the stand so that an air stream from a bottom of the cylinder could pass through the glass tubes. On the top of the cylinder for experimental use, a tubular transparent resin hood for observation having a diameter of 20 cm and a height of 30 cm was placed in such a manner that the tubular transparent resin hood and the cylinder matched their outer rims.

At the bottom of the cylinder, the pest control device in operation was placed. Then, a number of the female imagines of Culex pipiens pallens knocked down was counted over a period. A time (KT50 value) for knocking down 50% population of the female imagines of Culex pipiens pallens was measured. Further, the glass tubes were removed, then the operation of the air fan was measured thereafter. The same tests using other imagines of Culex pipiens pal lens were carried out after 500 hours, 600 hours, 700 hours and 800 hours since the beginning of the operation of the pest control device. The result is shown in Table 1.

TABLE 1

|                  | Time |       |       |       |       |
|------------------|------|-------|-------|-------|-------|
|                  | 0 h  | 500 h | 600 h | 700 h | 800 h |
| KT50 value (min) | 4.7  | 5.2   | 5.1   | 4.8   | >10   |
| Liquid level (cm)| 3.2  | 2.1   | 1.8   | 1.6   | 1.3   |

* "Liquid level" indicates the liquid level measured from the bottom of the bottle 3.
* "Time" indicates the time passed since the beginning of the measurement.
* Abbreviation: "min" stands for minute. "h" stands for hour.

The Table 1 shows that the efficacy of the pest control device in the experiment was ended between 700 hours and 800 hours. Moreover, the volatile loss of a solution consisting of tetradecane and pentadecane at a ratio of 6/4, which had been volatilized by 700 hours, is determined by the following equation:

$$(3.2-1.6)/3.2 \times 15 = 7.5 [ml].$$

Therefore, if the solution consisting of tetradecane and pentadecane at a ratio of 6/4 is set to be 7.5 ml, the amount of the solution in the bottle is zero at 700 hour time since the start of the operation of the pest control device used in the experiment, so that the end point of efficacy and the disappearance point of the solution are matched.

It should be noted that, the respective arrangements in accordance with the present embodiment may be employed appropriately in combination, and the present invention is not limited to the combinations described above.

As discussed above, a pest control device of the present embodiment, is provided with (1) a volatile substance holder, including a first and a second volatilization surfaces, the first volatilization surface holding a pest control component so that the pest control component can be volatilized into the air (i.e., the volatilization surface (I)), and the second volatilization surface being able to hold a liquid so that the liquid can be volatilized into the air (i.e., the volatilization surface (II)), where the pest control component and the liquid are volatile at ordinary temperature, and (2) an indicating means, including a liquid supplying means and a liquid containing means, the liquid supplying means supplying the liquid to the second volatilization surface (i.e., the volatilization surface (II)) of the volatile substance holder, and the liquid containing means containing the liquid to be supplied to the second volatilization surface (i.e., the volatilization surface (II)) via the liquid supplying means, wherein the indicating means indicates how much the pest control component to be volatilized from the first volatilization surface (i.e., the volatilization surface (I)) is left in the volatile substance holder by showing how much the liquid is left in the liquid containing means.

More specifically, the pest control device of the present embodiment is provided with (1) a pest control component holder for holding the pest control component so that the pest control component can be volatilized into the air, (2) the liquid holder for holding the liquid so that the liquid can be volatilized into the air, (3) the liquid supplying means for supplying the liquid to the liquid holder, (4) the liquid containing means for containing the liquid that is to be supplied to the liquid holder via the liquid supplying means, and (5) the indicating means for indicating how much the pest control component, which is volatilized from the pest control component holder, is left in the volatile substance holder, by showing how much the liquid is left in the liquid containing means, where the pest control component and the liquid are volatile at ordinary temperature. This arrangement attains a high efficiency in the controlling, while allowing the user to surely check the reduction and the end point of the pest control component.

It is preferable that the pest control device is provided with a pest control agent containing case that contains the pest control component holder and the liquid holder in, and exhausts the volatile components volatilized from the pest control component holder and the liquid holder to the outside, so that both the pest control component holder and the liquid holder are located in the same pest control agent containing case, for the purpose of having a higher interrelationship between the pest control component holder and the liquid holder.

Moreover, a pest control device is preferably further provided with an air stream generating means so as to generate an air stream for the volatilization of the pest control component and the liquid. It is preferable that the air stream generating means generates the air stream in a containing section for the pest control component holder and the liquid holder in the pest control agent containing case, in order to further improve the interrelationship between the pest control component holder and the liquid holder.

Because further provided is the air stream generating means for generating the air stream for the volatilization of the pest control component and the liquid, the air stream can be utilized for the volatilization of the pest control component and the liquid. This improves the interrelationship between the volatilization of the pest control component and that of the liquid. Therefore, it is possible to easily control the end (disappearance) points of the pest control component and the liquid.

Moreover, the pest control device is preferably arranged that the first and the second volatilization surfaces are provided on a same plane.

The above arrangement improves the interrelationship between the first and the second volatilization surfaces, because the first and the second volatilization surfaces are provided on a same plane. Especially, when the air stream is used for volatilizing the pest control component and the liquid, the above arrangement, where the first and the second volatilization surfaces are provided on a same plane, can disposed the first and the second volatilization surfaces in the equidistance from the air stream generator, thereby further improving the interrelationship between the first and the second volatilization surfaces.

Furthermore, the pest control device is preferably arranged that the liquid containing means is a container that is transparent or translucent.

The above arrangement allows the liquid containing means to be used as the indicator, thereby eliminating need for additional complicated system for indication, while lowering the manufacturing cost of the pest control device. Meanwhile, it is also possible to very easily check how much the liquid is left in the liquid containing means, that is, how much the pest control component is left.

It is preferable for the pest control device that the pest control component is a compound in a pyrethroid group, while it is more preferable for the pest control device that the pest control component is at least one of compounds selected from 2,3,5,6-tetrafluoro-4-methoxymethylbenzyl 3-(1-propenyl)-2,2-dimethylcyclopropanecarboxylate, 2,3, 5,6-tetrafluoro-4-methylbenzyl 3-(1-propenyl)-2,2-dimethylcyclopropanecarboxylate, and 2,3,5,6-tetrafluorobenzyl 3-(2,2-dichloroethenyl)-2,2-dimethylcyclopropanecarboxylate.

The above arrangement provides a pest control device excellent in the controlling activity and volatility of the pest control compound.

The pest control device is so arranged that volatile loss of the pest control component has a relationship with volatile loss of the liquid contained in the liquid containing means, by setting; a type of the pest control component and pest control component content thereof, a type of the liquid contained in the liquid containing means and quantity to use thereof, a ratio of a surface area of the volatilization surface (I) over that of the volatilization surface (II), a material of the volatilization surface (I) and a material of the volatilization surface (II).

The above arrangement makes it easy to control the end point and the volatile loss of the volatile components, thereby providing a pest control device that can perform a precise and subtle control of the end point.

The pest control device of the present embodiment may have an arbitral life time, to be used for 30 days, 60 days or even 100 days, while having the end point subtly controlled and an exact indication function.

Moreover, the volatile substance holder of the present embodiment is a volatile substance holder for use in the pest control device, and the volatile substance holder is provided with a first and a second volatilization surfaces, the first volatilization surface holding a pest control component so that the pest control component can be volatilized into the air, and the second volatilization surface being able to hold a liquid so that the liquid can be volatilized into the air, where the pest control component and the liquid are volatile at ordinary temperature, while further including a compartment in a boundary area between the first and the second volatilization surfaces, so that the first and the second volatilization surface are separated so as not to touch each other but in a same plane.

With the above arrangement, it is possible to provide a volatile substance holder that holds the pest control component as well as the liquid for indicating the reduction and the end point of the pest control component, thereby providing the pest control device with an excellent pest controlling efficacy. Moreover, the arrangement, where the first and the second volatilization surfaces are disposed on a same plane, further improves the interrelationship between the first and the second volatilization surfaces, that is, the interrelationship between the pest control component holder and the liquid holder. Moreover, because the first and the second volatilization surfaces are separated in the above arrangement, it is possible to provide a pest control device in which the liquid and the pest control component do not to touch each other. Such pest control device is excellent in volatilization of the pest control component, thereby optimizing the efficiency of the pest control.

It is preferable that the volatile substance holder holds the a compound in the pyrethroid group in the volatilization surface (1), so that it is possible to provide the pest control device is excellent in volatilization of the pest control component, thereby optimizing the efficiency of the pest control.

The invention being thus described, it will be obvious that the same way may be varied in many ways. Such variations are not to be regarded as a departure from the spirit and scope of the invention, and all such modifications as would be obvious to one skilled in the art are intended to be included within the scope of the following claims.

What is claimed is:

1. A pest control device, comprising:

a volatile substance holder, including a first and a second volatilization surfaces, said first volatilization surface holding a pest control component so that said pest control component can be volatilized into the air, and said second volatilization surface being able to hold a liquid so that said liquid can be volatilized into the air, where said pest control component and said liquid are volatile at ordinary temperature; and indicating means, including liquid supplying means and liquid containing means, said liquid supplying means supplying said liquid to said second volatilization surface of said volatile substance holder, and said liquid containing means containing said liquid to be supplied to said second volatilization surface via said liquid supplying means, wherein said indicating means indicates how much said pest control component to be volatilized from said first volatilization surface is left in said volatile substance holder by showing how much the liquid is left in said liquid containing means.

2. A pest control device as set forth in claim 1, further comprising air stream generating means so as to generate an air stream for the volatilization of said pest control component and said liquid.

3. The pest control device as set forth in claim 2, wherein said volatile substance holder is provided on an air inlet side of said air stream generating means, so that said air stream generating means inhales volatile components volatilized from said first and said second volatilization surfaces of said volatile substance holder so as to exhaust said volatile components to an exterior.

4. The pest control device as set forth in claim 1, wherein said first and said second volatilization surfaces are separated so as not to touch each other.

5. The pest control device as set forth in claim 1, wherein said first and said second volatilization surfaces are provided on a same plane.

6. The pest control device as set forth in claim 5, further comprising:

a compartment in a boundary area between said first and said second volatilization surfaces.

7. The pest control device as set forth in claim 1, wherein said first and said second volatilization surfaces have a net-like or a honeycomb-like shape.

8. The pest control device as set forth in claim 1, wherein said liquid containing means is a container that is transparent or translucent.

9. The pest control device as set forth in claim 1, wherein said liquid supplying means is an absorbent material that is suspended in said liquid containing means so as to absorb said liquid in said liquid containing means and to supply said liquid to said second volatilization surface which said absorbent material touches.

10. The pest control device as set forth in claim 1, wherein said pest control component is a compound in a pyrethroid group.

11. The pest control device as set forth in claim 10, wherein said pest control component is at least one of compounds selected from 2,3,5,6-tetrafluoro-4-methoxymethylbenzyl 3-(1-propenyl)-2,2-dimethylcyclopropanecarboxylate, 2,3,5,6-tetrafluoro-4-methylbenzyl 3-(1-propenyl)-2,2-dimethylcyclopropane carboxylate, and 2,3,5,6-tetrafluorobenzyl 3-(2,2-dichloroethenyl)-2,2-dimethylcyclopropanecarboxylate.

12. A volatile substance holder for use in the pest control device as set forth in claim 1, comprising:

a first and a second volatilization surfaces, said first volatilization surface holding a pest control component so that said pest control component can be volatilized into the air, and said second volatilization surface being able to hold a liquid so that said liquid can be volatilized into the air, where said pest control component and said liquid are volatile at ordinary temperature.

13. The volatile substance holder as set forth in claim 12, wherein said first and said second volatilization surfaces are separated so as not to touch each other.

14. The volatile substance holder as set forth in claim 12, wherein said first and said second volatilization surfaces are provided on a same plane.

15. The volatile substance holder as set forth in claim 14, further comprising:

a compartment in a boundary area between said first and said second volatilization surfaces.

16. The volatile substance holder as set forth in claim 12, wherein said first and said second volatilization surfaces have a net-like or a honeycomb-like shape.

* * * * *